US011266505B2

(12) United States Patent
Jacobsen et al.

(10) Patent No.: US 11,266,505 B2
(45) Date of Patent: Mar. 8, 2022

(54) SACRO-ILIAC (SI) JOINT FIXATION SYSTEM AND METHOD

(71) Applicant: CTL Medical Corporation, Addison, TX (US)

(72) Inventors: Walter P. Jacobsen, Milwaukee, WI (US); Jon Suh, Ambler, PA (US); Rob Trezise, Coatesville, PA (US); Sean Suh, Milltown, NJ (US)

(73) Assignee: CTL Medical Corporation, Addison, TX (US)

( * ) Notice: Subject to any disclaimer, the term of this patent is extended or adjusted under 35 U.S.C. 154(b) by 0 days.

(21) Appl. No.: 16/797,861

(22) Filed: Feb. 21, 2020

(65) Prior Publication Data

US 2020/0268518 A1 Aug. 27, 2020

Related U.S. Application Data

(60) Provisional application No. 62/809,419, filed on Feb. 22, 2019.

(51) Int. Cl.
*A61F 2/30* (2006.01)
*A61F 2/44* (2006.01)

(52) U.S. Cl.
CPC ........ *A61F 2/30988* (2013.01); *A61F 2/4455* (2013.01); *A61F 2002/3085* (2013.01); *A61F 2002/30405* (2013.01); *A61F 2002/30622* (2013.01); *A61F 2002/30736* (2013.01); *A61F 2002/30995* (2013.01)

(58) Field of Classification Search
CPC .......... A61F 2/4455; A61F 2002/30995; A61F 2/30988
See application file for complete search history.

(56) References Cited

U.S. PATENT DOCUMENTS

| | | | | |
|---|---|---|---|---|
| 5,702,453 A | * | 12/1997 | Rabbe | A61F 2/30744 623/17.16 |
| 9,700,356 B2 | * | 7/2017 | Donner | A61B 17/1742 |
| 2012/0191191 A1 | * | 7/2012 | Trieu | A61B 17/8665 623/17.11 |
| 2020/0155324 A1 | * | 5/2020 | Sazy | A61F 2/4455 |

* cited by examiner

*Primary Examiner* — Christian A Sevilla
(74) *Attorney, Agent, or Firm* — Brainspark Associates, LLC

(57) ABSTRACT

Disclosed is a sacro-iliac join fusion system including a block or wedging cage positioned between the sacrum and iliac bone, wherein the block or wedging cage can fit around one or more fixation or axial screws to fasten the block or wedging cage and secure the block or wedging cage to the adjacent pelvic bones to promote fusion and fixation.

20 Claims, 41 Drawing Sheets

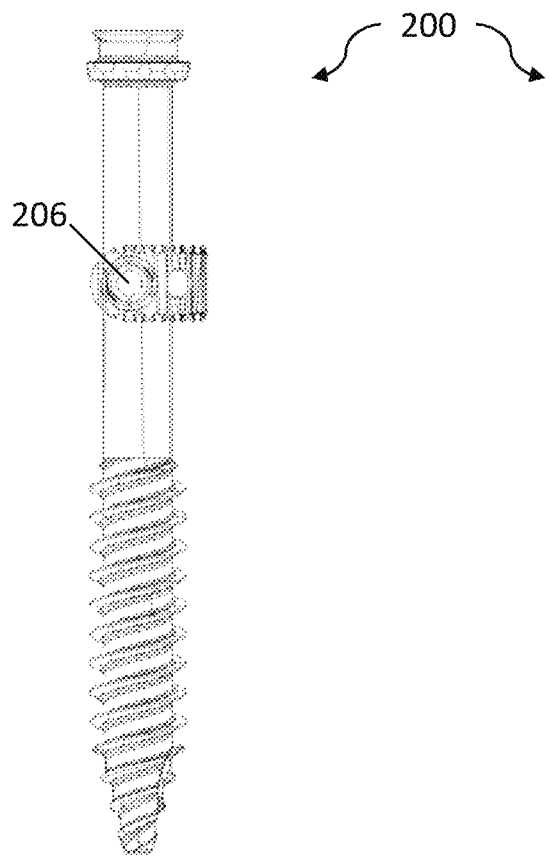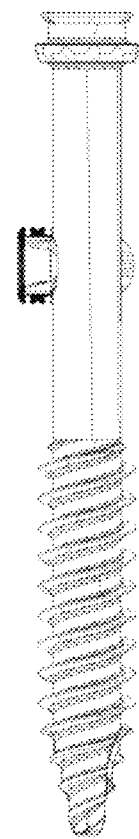
FIG. 2C  FIG. 2D
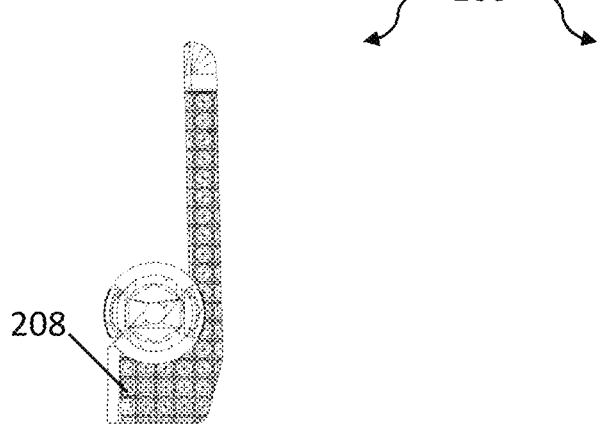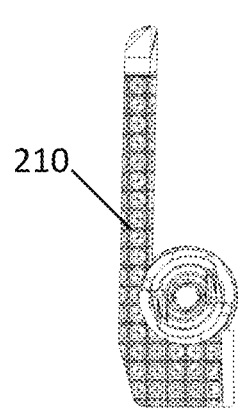
FIG. 2E  FIG. 2F

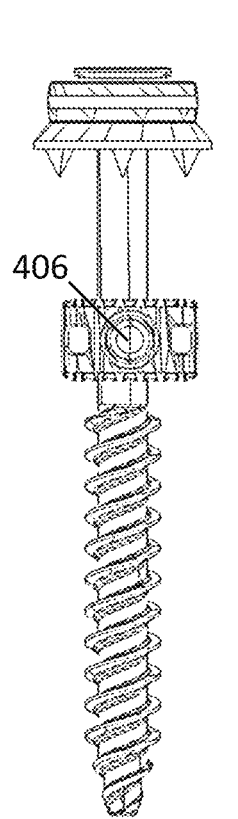
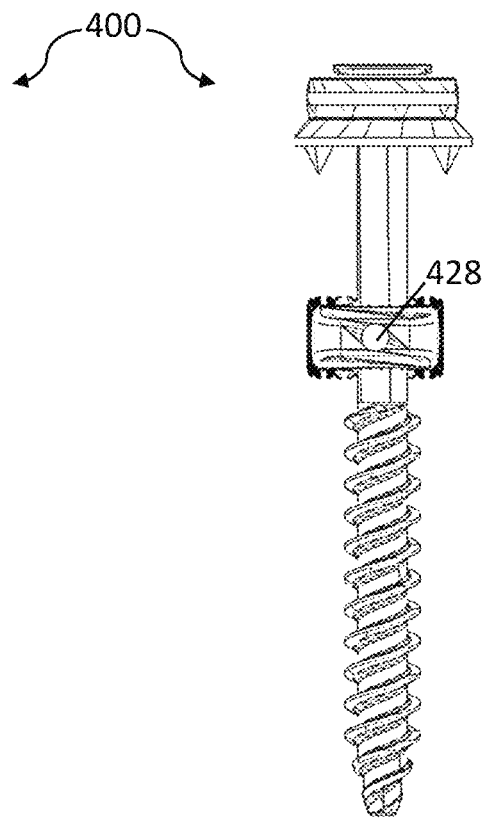
FIG. 4C	FIG. 4D
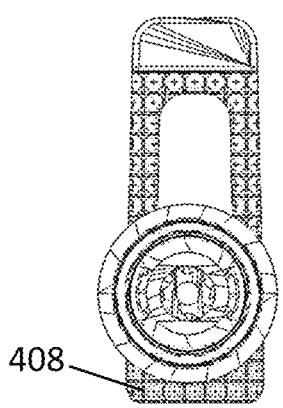
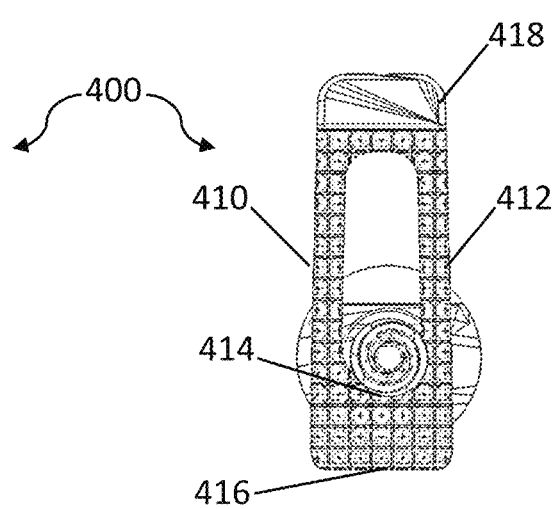
FIG. 4E	FIG. 4F

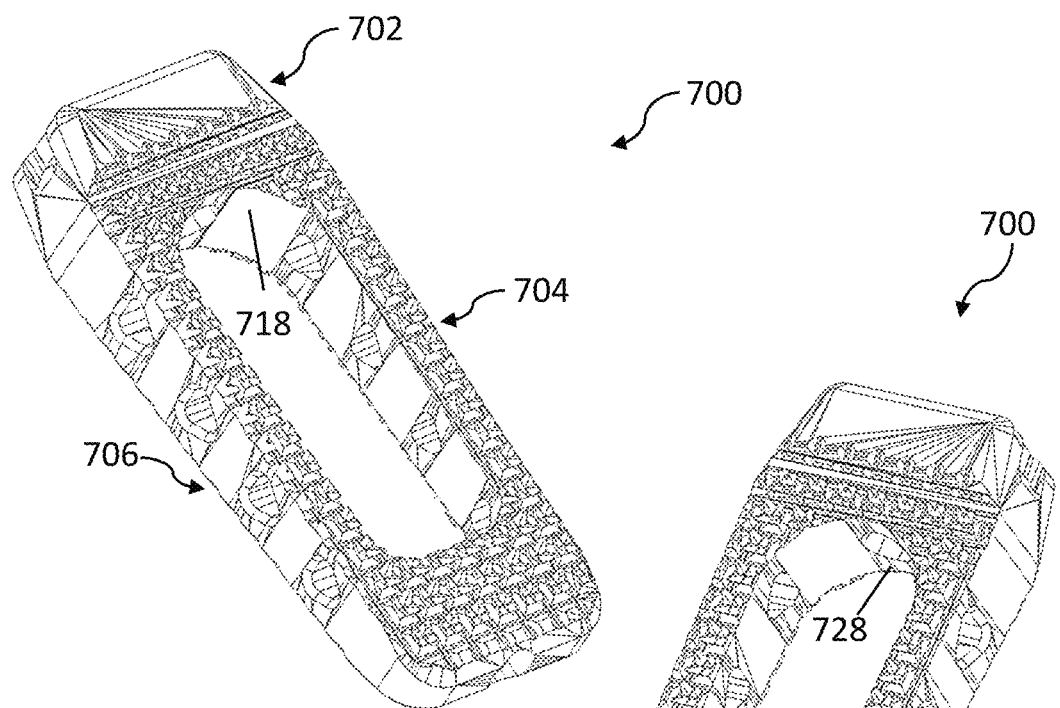
FIG. 7A
FIG. 7B
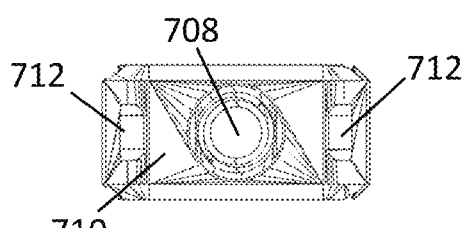
FIG. 7C
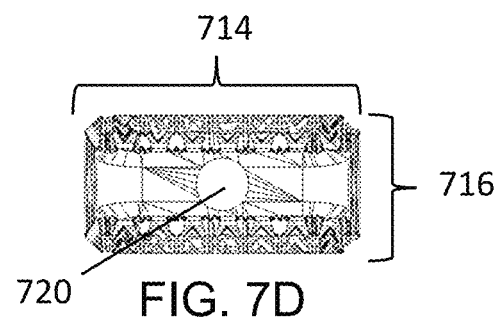
FIG. 7D

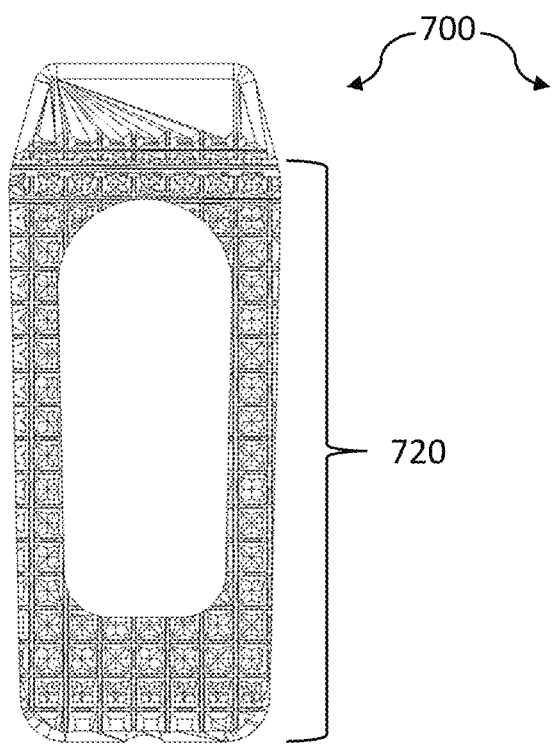
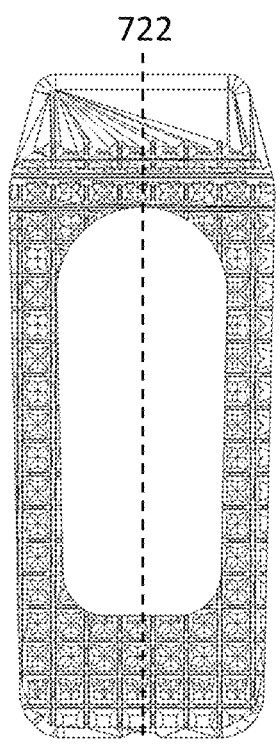
FIG. 7E    FIG. 7F
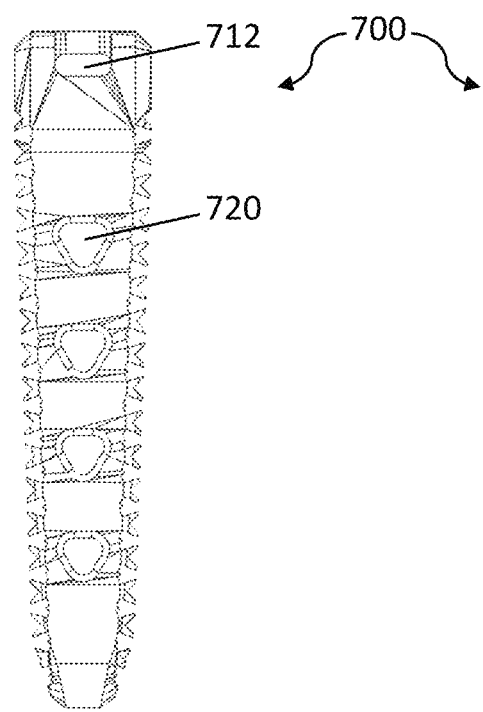
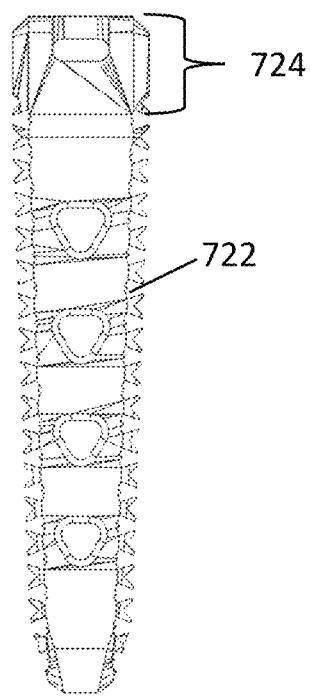
FIG. 7G    FIG. 7H

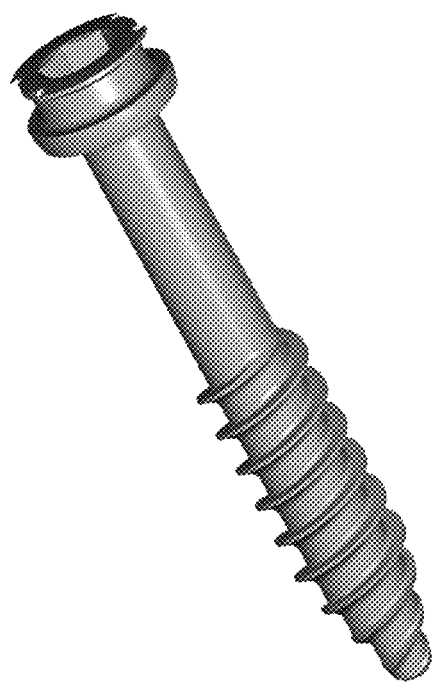
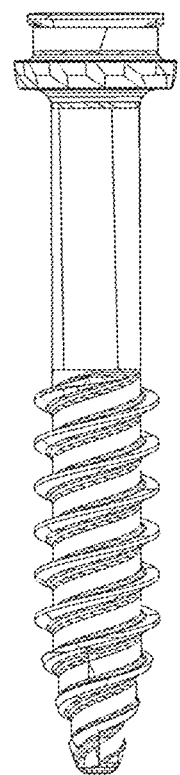
FIG. 13A  FIG. 13B
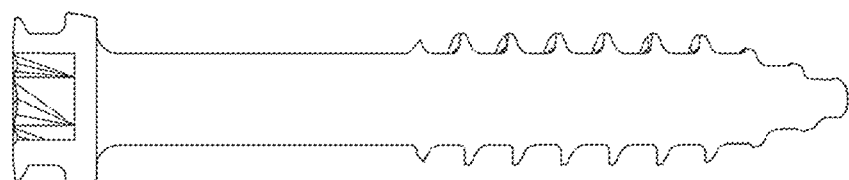
FIG. 13C
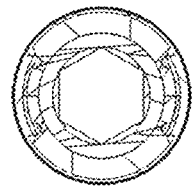
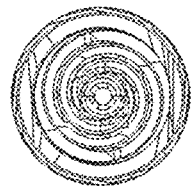
FIG. 13D  FIG. 13E

1902

1904

1906

1908

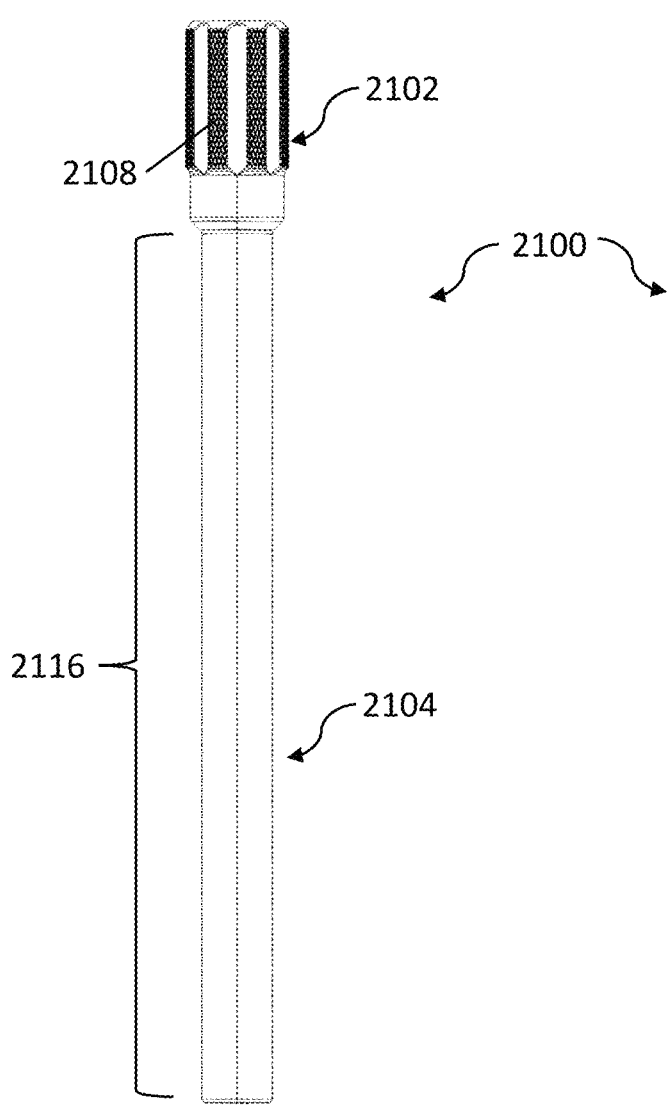
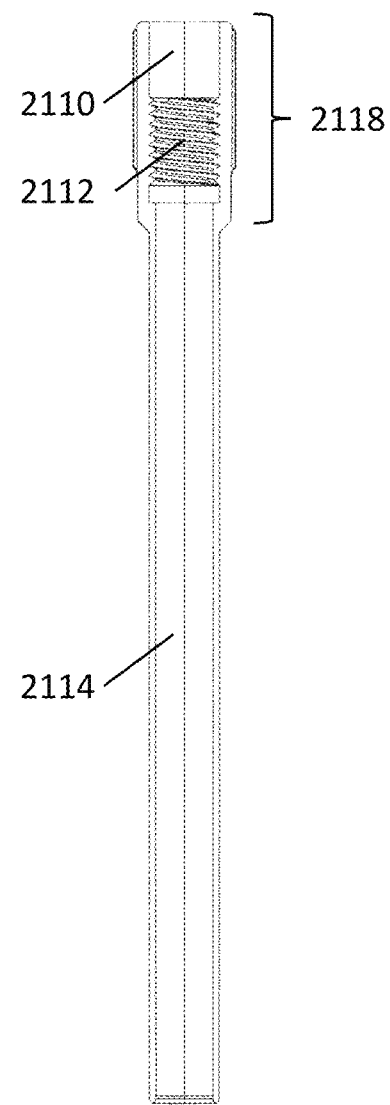
FIG. 21A  FIG. 21B
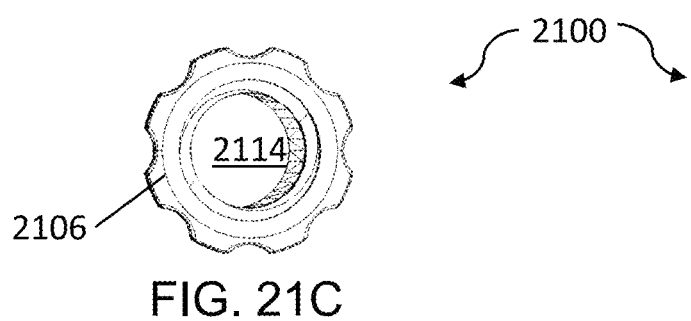
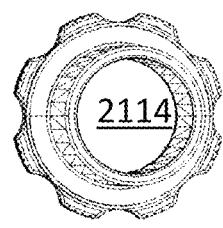
FIG. 21C  FIG. 21D

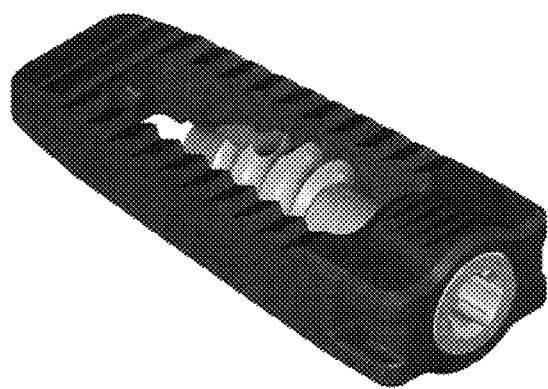
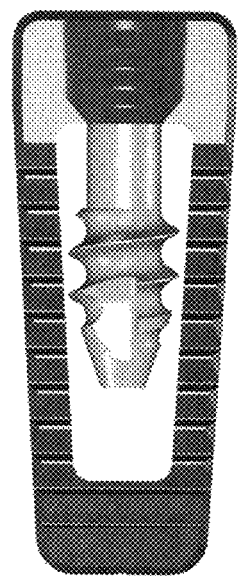
FIG. 23A     FIG. 23B
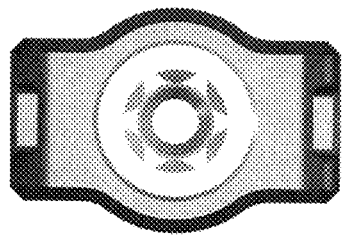
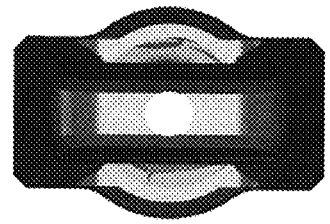
FIG. 23C     FIG. 23D

SACRO-ILIAC (SI) JOINT FIXATION SYSTEM AND METHOD

CROSS-REFERENCE TO RELATED APPLICATIONS

This application claims the benefit of U.S. Provisional Application No. 62/809,419 entitled "Wedging Plate," filed Feb. 22, 2019, the disclosure of which is incorporated by reference herein in its entirety.

TECHNICAL FIELD

The present invention relates to methods, devices, and systems for an improved wedging cage within the sacroiliac (SI) joint. More specifically, the improved wedging cage may allow the implantation of the wedging cage before screws are deployed and after screws are deployed.

BACKGROUND OF THE INVENTION

Low back pain (LBP) is exceedingly common in modern society, affecting well over 90% of adults at some point in their lives. Loss of productivity and income combined with medical expenses results in vast expenditures annually in the US related to low back pain. Successful treatment of low back pain demands identifying the pain generator(s), which can be a significant challenge due to the multifactorial nature of this condition.

Traditionally doctors have diagnosed herniated discs and facet joints as primary pain generators, but recently there has been a resurgence in consideration of the SI joint as a low back pain generator. Despite the large number of patients with SI joint pain, treatment options have been limited to conservative care involving physical therapy and joint injections, and if conservative therapy fails, then SI joint fusion surgery is recommended.

However, the current SI fusion implants do not provide flexibility to the doctor during the operative procedure. The doctor must typically choose between screws or cages in an attempt to fuse or fixate the bone surfaces together. Therefore, a need exists to provide an implant system that provides flexibility to use a combination of implants and/or implant components, as well as an implant that can adapt to operative changes to allow both fusion and fixation together.

BRIEF SUMMARY OF THE INVENTION

The following presents a simplified summary of the subject matter in order to provide a basic understanding of some aspects of the subject matter. This summary is not an extensive overview of the subject matter. It is intended to neither identify key or critical elements of the subject matter nor delineate the scope of the subject matter. Its sole purpose is to present some concepts of the subject matter in a simplified form as a prelude to the more detailed description that is presented later.

In accordance with various aspects of the present subject matter, an SI joint fixation system comprises an A-shaped, a B-shaped, a C-shaped, H-shaped, I-shaped, L-shaped, O-shaped, U-shaped, a Y-shaped, and M or W shaped wedging cage and/or any combination thereof. The SI joint fixation system further comprises a screw. The screw includes a fixation screw or an axial screw. The fixation screw is intended to be positioned or deployed perpendicular or substantially perpendicular to the axis of the wedging cage. The axial screw is intended to be positioned or deployed parallel or substantially parallel to the axis of the wedging cage or in alignment with the axis of the bore or threaded bore. The SI joint fixation system may further comprise a delivery instrument. The delivery instrument includes a sleeve, an insertion cannula.

The SI joint fixation system comprises an L-shaped or I-shaped wedging cage. The L-shaped and/or I-shaped wedging cage may comprise a base and at least one longitudinal member. The base can include a threaded bore, a top surface and a bottom surface, the threaded bore extending from a top surface through the bottom surface. At least one longitudinal member can extend from a bottom surface of the base. The at least one longitudinal member may extend perpendicularly or substantially perpendicular from the base, the term substantially perpendicular include a variety of angulations, including 0.25 degrees to 10 degrees from neutral. The at least one longitudinal member may include at least a portion of at least one bone contacting surface have a smooth surface or a textured surface, the textured surface may comprise grit blasting, acid etching, laser texturing, wave structures, pyramidal structures, reverse pyramidal structures and/or any combination thereof. The SI joint fixation system may further comprise a screw, the screw comprising a head, a shaft and a thread. The screw can be sized and configured to be inserted within the threaded bore. Alternatively, the bottom surface of the base and a portion of the at least one longitudinal member can be sized and configured to receive the screw. The at least one longitudinal member may be positioned adjacent to a circumference of the threaded bore. Alternatively, the at least one longitudinal member may be aligned with a longitudinal axis of the threaded bore.

In another embodiment, the SI joint fixation system comprises a U-shaped wedging cage. The U-shaped wedging cage comprises a base, a first longitudinal member and a second longitudinal member. The base including a threaded bore, a top surface and a bottom surface, the threaded bore extending from a top surface through the bottom surface. The first longitudinal member and the second longitudinal member spaced apart and extending from the bottom surface of the base. The first and/or second longitudinal member extending perpendicularly or substantially perpendicular from the base, the substantially perpendicular includes 0.25 degrees to 10 degrees from neutral. The first and/or second longitudinal member including at least a portion of the at least one bone contacting surface have a smooth surface or a textured surface, the textured surface comprises grit blasting, acid etching, laser texturing, wave structures, pyramidal structures, reverse pyramidal structures and/or any combination thereof. The SI joint fixation system may further comprise a screw, the screw comprises a head, a shaft and a thread. The screw is sized and configured to be inserted within the threaded bore and/or the through-hole. Alternatively, the bottom surface of the base and a portion of the first and second longitudinal member is sized and configured to receive the screw.

In another embodiment, the SI joint fixation system comprises an O-shaped wedging cage. The wedging cage comprises a first base, a second base, a first longitudinal member and a second longitudinal member. The first base including a threaded bore, a top surface and a bottom surface, the threaded bore extending from a top surface through the bottom surface. The second base including a through-hole, the through-hole of the second base is aligned with and/or concentrically aligned with the threaded bore of the first base. The first longitudinal member and the second longitudinal member spaced apart and extending between the first base and the second base. The first and/or second longitudinal member extending perpendicularly or substantially perpendicular from the base, the substantially perpendicular includes 0.25 degrees to 10 degrees from neutral. The first and/or second longitudinal member including at least a portion of the at least one bone contacting surface have a smooth surface or a textured surface, the textured surface comprises grit blasting, acid etching, laser texturing, wave structures, pyramidal structures, reverse pyramidal structures and/or any combination thereof. The SI joint fixation system may further comprise a screw, the screw comprises a head, a shaft and a thread. The screw is sized and configured to be inserted within the threaded bore and/or the through-hole. Alternatively, the bottom surface of the base and a portion of the first and second longitudinal member is sized and configured to receive the screw.

In another embodiment, the SI joint fixation system comprises a H-shaped wedging cage. The H-shaped wedging cage comprises a base, a first longitudinal member and a second longitudinal member. The base including a threaded bore, a top surface and a bottom surface, the threaded bore extending from a top surface through the bottom surface. Each of the first longitudinal member and the second longitudinal member having a longitudinal axis, a first end and a second end. The first longitudinal member and the second longitudinal member spaced apart. The first and/or second longitudinal member extending perpendicularly or substantially perpendicular from the base, the substantially perpendicular includes 0.25 degrees to 10 degrees from neutral. The base positioned between the first end and second end of the first and second longitudinal member. The first and/or second longitudinal member including at least a portion of the at least one bone contacting surface have a smooth surface or a textured surface, the textured surface comprises grit blasting, acid etching, laser texturing, wave structures, pyramidal structures, reverse pyramidal structures and/or any combination thereof. The SI joint fixation system may further comprise a screw, the screw comprises a head, a shaft and a thread. The SI joint fixation system may further comprise a screw, the screw comprises a head, a shaft and a thread. The screw is sized and configured to be inserted within the threaded bore and/or the through-hole. Alternatively, the bottom surface of the base and a portion of the first and second longitudinal member is sized and configured to receive the screw.

In another embodiment, the SI joint fixation system comprises an anchored wedging cage. The anchored wedging cage comprises a wedging cage and an anchor assembly. The wedging cage may comprise an A-shaped, a B-shaped, a C-shaped, H-shaped, I-shaped, L-shaped, O-shaped, U-shaped, a Y-shaped, and M or W shaped wedging cage and/or any combination thereof. The wedging cage may comprise at least one base, the at least one base includes a threaded bore. The anchor assembly comprises a plurality of pins and an anchor. The anchor comprises a shaft and at least two blades, the shaft comprising a channel, the channel is disposed around the circumference of the shaft. The channel is sized and configured to receive a portion of the plurality of pins. The anchor assembly is rotatable from an unlocked position to a locked position, the unlocked position has the at least a portion of the anchor mating with a portion of the wedging cage and it allows the wedging cage to move or slide within the SI joint. The locked position rotates the anchor anywhere between 1 degree to 90 degrees away from the portion of the wedging cage and allows the wedging cage to lock into place within the SI joint.

In another embodiment, the SI joint fixation system comprises a shelled wedging cage and bone growth block. The shell wedging cage comprises a first base, a second base, a first longitudinal member and a second longitudinal member. The first base including a bore, a top surface and a bottom surface, the bore extending from a top surface through the bottom surface. The first longitudinal member and the second longitudinal member spaced apart and extending between the first base and the second base. The first and/or second longitudinal member extending perpendicularly or substantially perpendicular from the first and/or second base, the substantially perpendicular includes 0.25 degrees to 10 degrees from neutral. The first and/or second longitudinal member including at least a portion of the at least one bone contacting surface have a smooth surface or a textured surface, the textured surface comprises grit blasting, acid etching, laser texturing, wave structures, pyramidal structures, reverse pyramidal structures and/or any combination thereof. The spacing apart of the first and second longitudinal member is sized and configured to receive the bone growth block.

In another embodiment, the SI joint fixation system comprises a shell wedging cage and a bone growth block. The shell wedging cage comprises a first base and a first longitudinal member, the first longitudinal member extending away from the first base. At least one surface of the first base and the first longitudinal member having a channel. The channel is sized and configured to receive a portion of the both growth block. The SI joint fixation system further comprises a screw, the screw is a fixation screw and/or an axial screw.

In another embodiment the SI joint fixation system may comprise a 3D printed wedging cage. The 3D printed wedging cage may comprise an A-shaped, a B-shaped, a C-shaped, H-shaped, I-shaped, L-shaped, O-shaped, U-shaped, a Y-shaped, and M or W shaped wedging cage and/or any combination thereof. At least a portion of the 3D printed wedging cage comprises porosity. The porosity may include a plurality of connected, interstitial pores uniformly or non-uniformly distributed throughout the entire wedging cage. The interstitial pores may match or substantially match trabecular or cortical patterns. Alternatively, the interstitial pores may have a shape, the shape may comprise a circle, an oval, a regular polygon or irregular polygon shape. The SI joint fixation system further comprises a screw, the screw is a fixation screw and/or an axial screw.

BRIEF DESCRIPTION OF THE SEVERAL VIEWS OF THE DRAWINGS

The following description and the annexed drawings set forth in detail certain illustrative aspects of the subject matter. These aspects are indicative, however, of but a few of the various ways in which the principles of the subject matter may be employed and the present subject matter is intended to include all such aspects and their equivalents. Other objects, advantages and novel features of the subject matter will become apparent from the following detailed description of the subject matter when considered in conjunction with the drawings.

FIGS. 2A-2H depict various views of one embodiment of an L-shaped wedging cage system;

FIGS. 4A-4H depict various views of one embodiment of an O-shaped wedging cage system;

FIGS. 7A-7H depict various views of one embodiment of an O-shaped wedging cage;

FIGS. 13A-13E depict various views of an alternative embodiment of a screw;

FIGS. 21A-21D depict various views of one embodiment of a sleeve;

FIGS. 23A-23D depict various views of one embodiment of an axial threaded anchor wedging cage;

DETAILED DESCRIPTION OF THE INVENTION

Figure 1A:
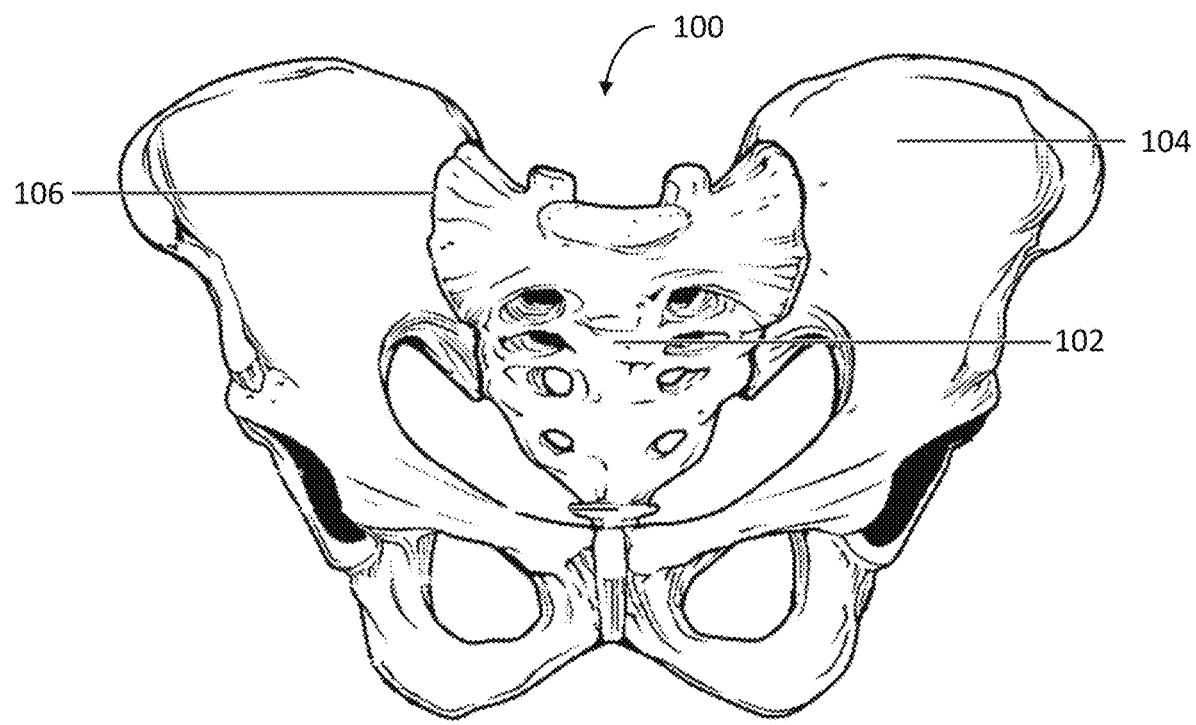
FIGS. 1A-1B illustrates one embodiment of the pelvic bones, namely the sacroiliac joint.

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The terms "including," "comprising" and variations thereof, as used in this disclosure, mean "including, but not limited to," unless expressly specified otherwise. The terms "a," "an," and "the," as used in this disclosure, mean "one or more," unless expressly specified otherwise.

Devices and/or device components that are disclosed in communication with each other need not necessarily be in continuous communication with each other, unless expressly specified otherwise. In addition, devices that are in direct contact with each other may contact each other directly or indirectly through one or more intermediary articles or devices. The device(s) disclosed herein may be made of a material such as silicon nitride, which may alternatively be combined, in various embodiments, with other materials such as, for example, a polymer, a metal, an alloy, or the like. For instance, the device(s) may comprise silicon nitride, alone or in combination with a Polyether Ether Ketone (PEEK), titanium, a titanium alloy, or the like, or various combinations of the foregoing. The material may be formed by a process such as, for example, an active reductive process of a metal (e.g., titanium or titanium alloy) to increase the amount of nanoscaled texture to device surface(s), so as to increase promotion of bone growth and fusion.

Although process steps, method steps, or the like, may be described in a sequential order, such processes and methods may be configured in alternate orders. In other words, any sequence or order of steps that may be described does not necessarily indicate a requirement that the steps be performed in that order. The steps of the processes or methods described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device or article may be alternatively embodied by one or more other devices or articles which are not explicitly described as having such functionality or features.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various devices, systems and methods for treating various anatomical structures of the spine and/or sacrum and/or other areas of human and/or animal bodies. While the disclosed embodiments may be particularly well suited for use during surgical procedures for the repair, fixation and/or support of sacral anatomy and the spine, it should be understood that various other anatomical locations of the body may benefit from various features of the present invention. Various surgical methods for preparing anatomical surfaces and/or for implanting or placement of the various devices and/or components described herein are also described, including the insertion and placement of implants between adjacent structures and/or portions thereof of the spine and/or sacrum, as well as within bones and/or between other joint surfaces.

In accordance with another aspect of the present subject matter, various methods for manufacturing devices and/or components thereof, as set for within any of the details described with the present application, are provided.

If desired, implants can be constructed from a variety of modular components, including modular components comprising different materials. If desired, such modular components could be provided in a kit form for selection and/or assembly in a surgical theatre and/or in situ during a surgical procedure. If desired, various components may be removable and replaceable.

The present subject matter will now be described with reference to the drawings, wherein like reference numerals are used to refer to like elements throughout. It is to be appreciated that the various drawings are not necessarily drawn to scale from one figure to another nor inside a given figure, and in particular that the size of the components may be arbitrarily drawn for facilitating the understanding of the drawings. In the following description, for purposes of explanation, numerous specific details are set forth in order to provide a thorough understanding of the present subject matter. It may be evident, however, that the present subject matter can be practiced without these specific details. Additionally, other embodiments of the subject matter are possible and the subject matter is capable of being practiced and carried out in ways other than as described. The terminology and phraseology used in describing the subject matter is employed for the purpose of promoting an understanding of the subject matter and should not be taken as limiting.

In accordance with various aspects of the present subject matter, a SI joint fixation system is disclosed which help reduce the symptoms caused by sacroiliac dysfunction, and provide the flexibility to surgeons during the operative procedure—in which surgeons are typically currently limited to choose between fusion or fixation. The SI joint wedging cage system addresses a variety of concerns by allowing the surgeon to adapt hybrid strategies such as fixation alone (screws or similar hardware), fusing alone, and/or fixation plus fusion together. The fixation plus fusion together is advantageous because the SI joint is acutely stabilized allowing long-term immobility as a result of adherence to the transfixing implant and the bone growth within the SI joint itself.

Figure 1B:
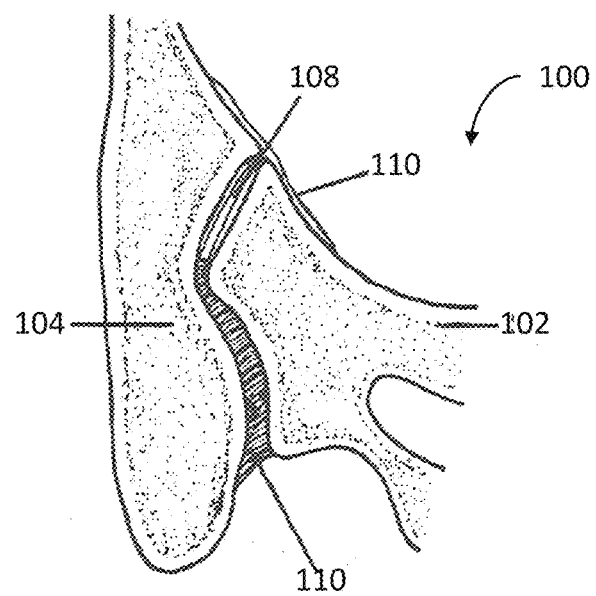
Figure 2A:
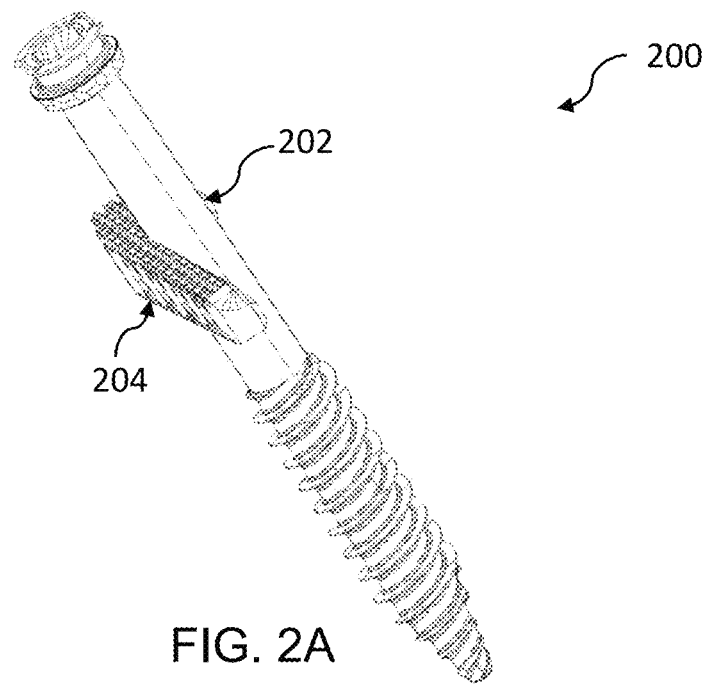
Figure 2B:
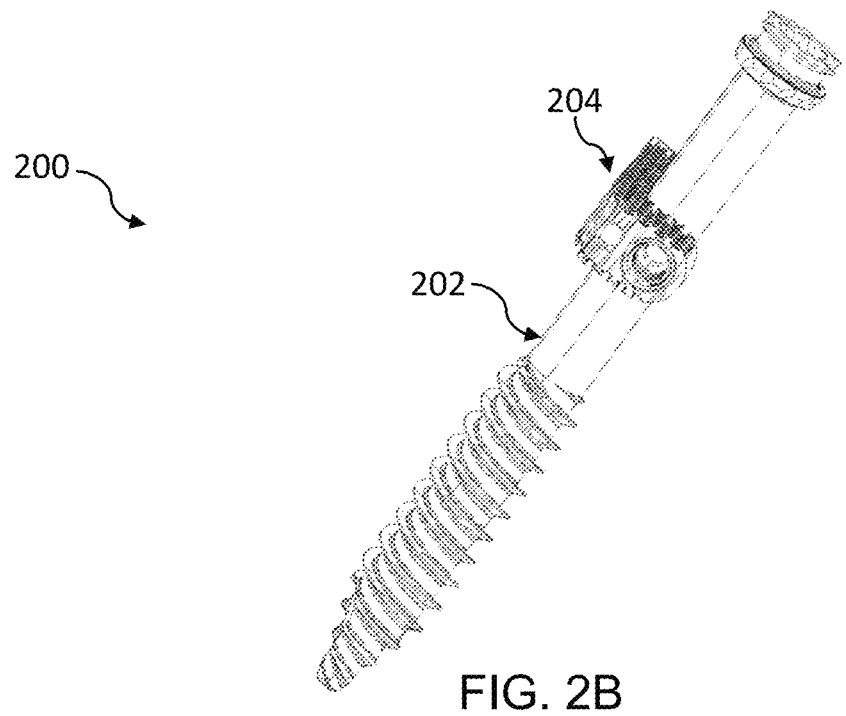
Figures 2G, 2H:
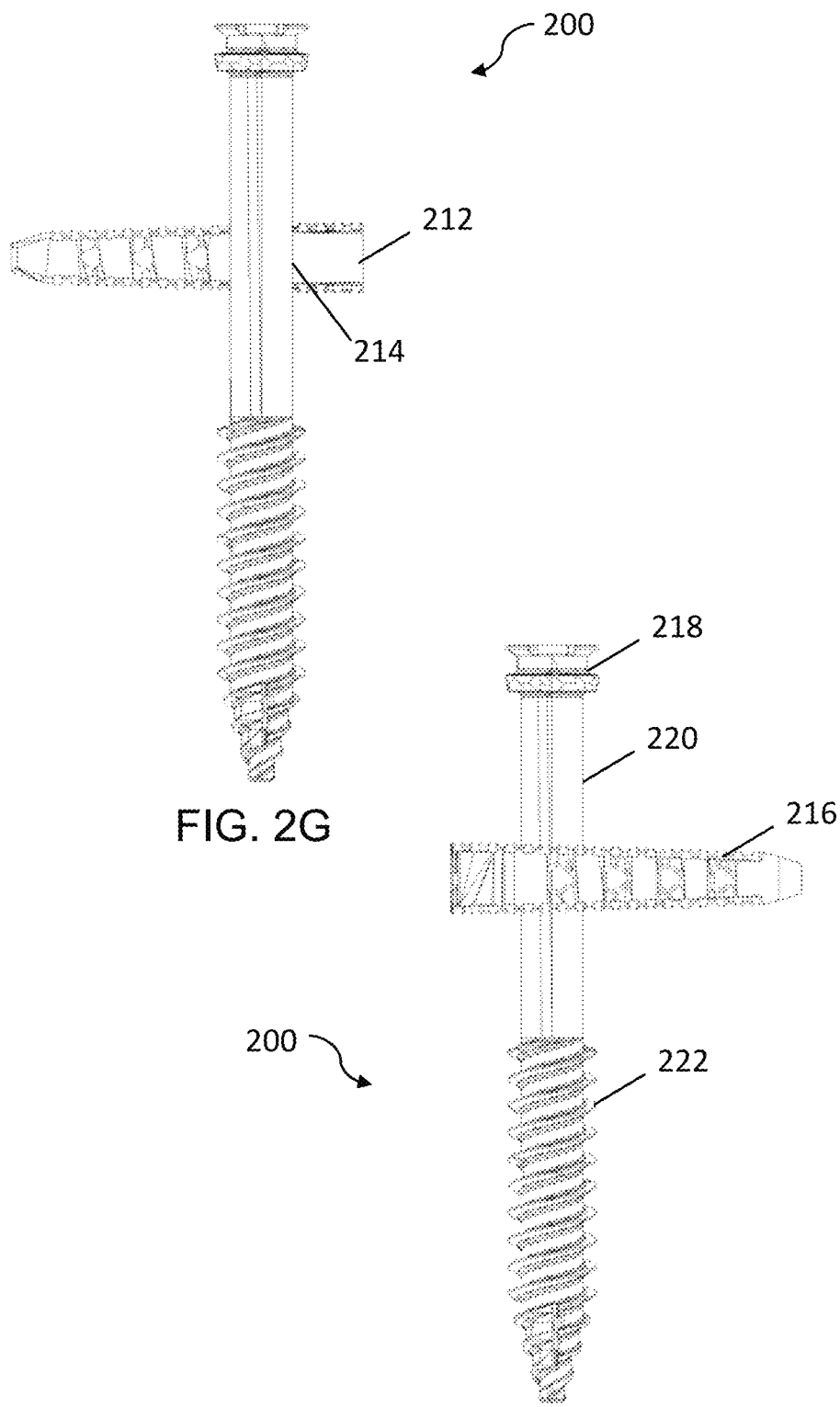
Figure 3A:
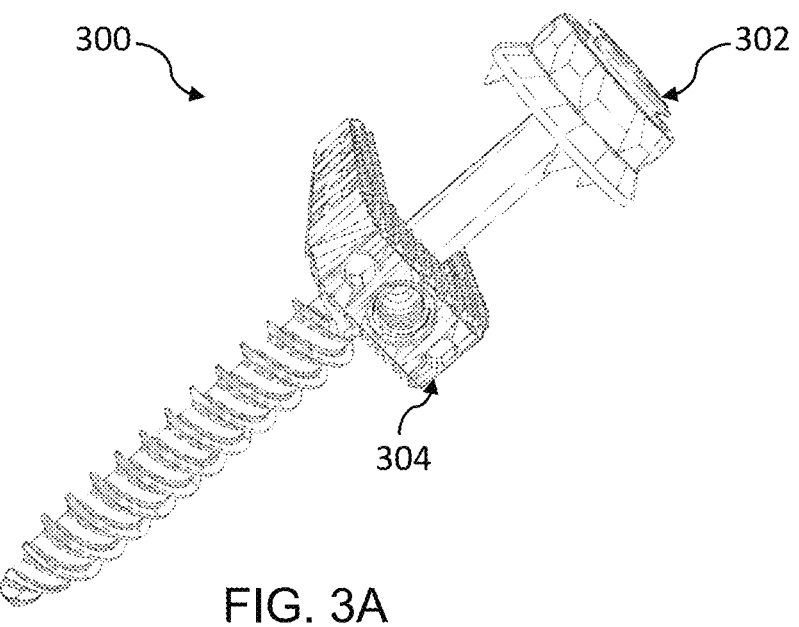
FIGS. 3A-3H depict various views of one embodiment of a U-shaped wedging cage system.
Figure 3B:
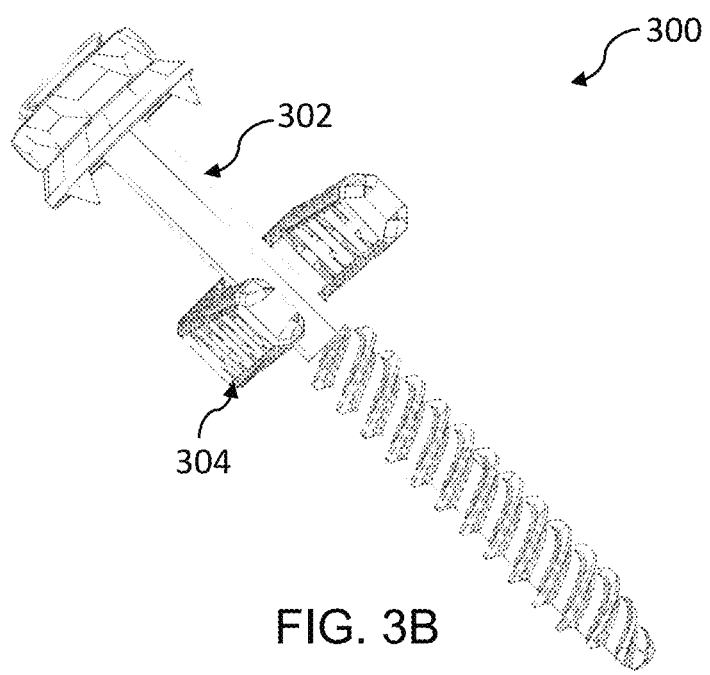
Figure 3C:
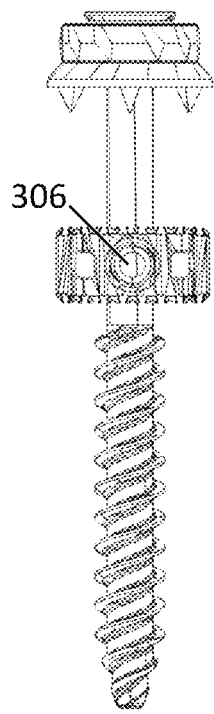
Figure 3D:
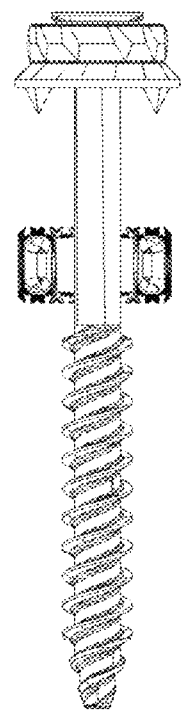
Figure 3E:
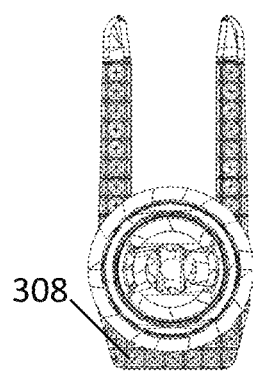
Figure 3F:
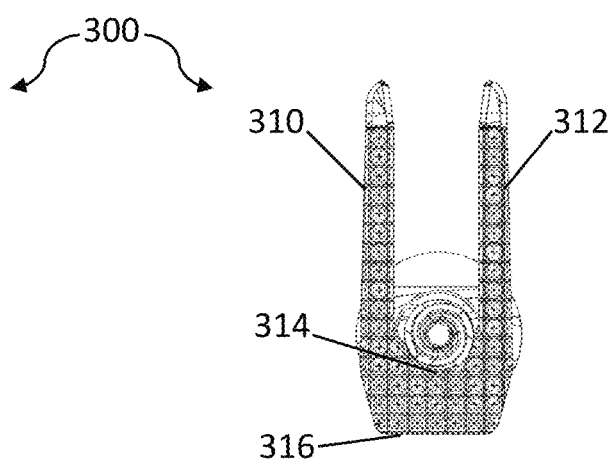
Figure 3G:
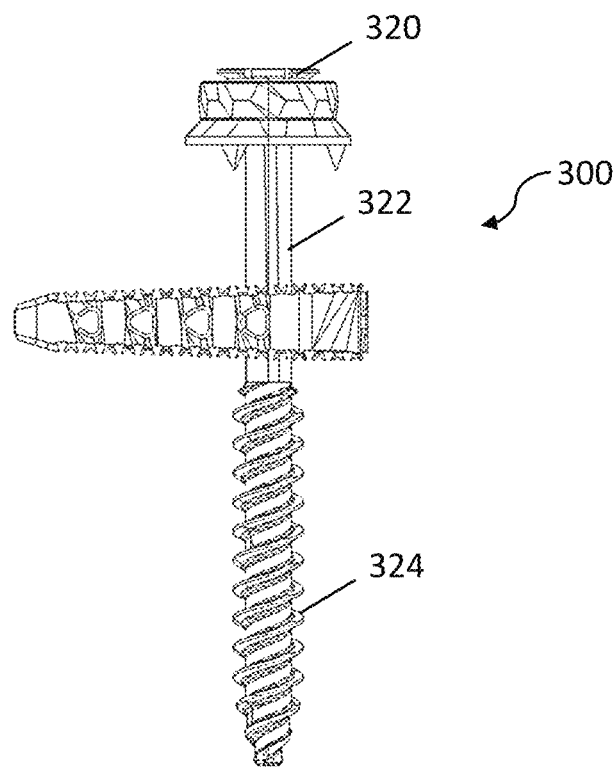
Figure 3H:
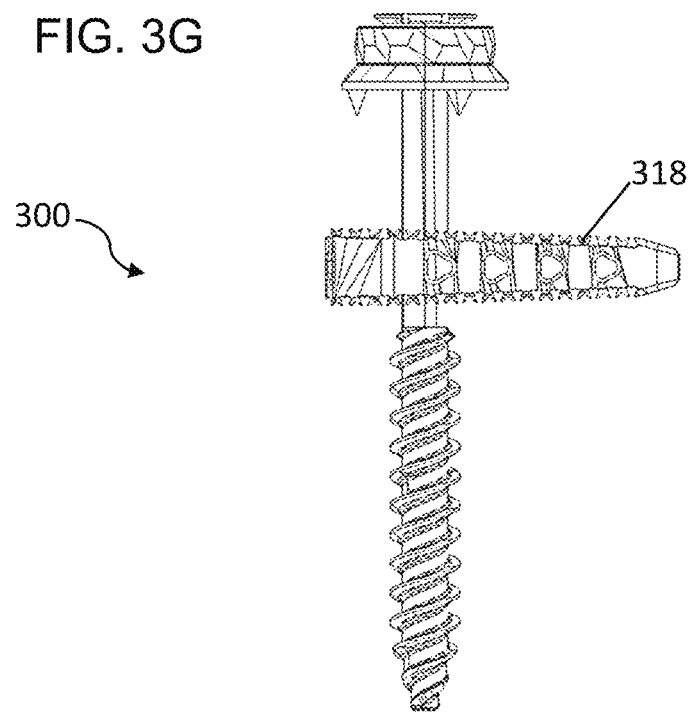
Figure 4A:
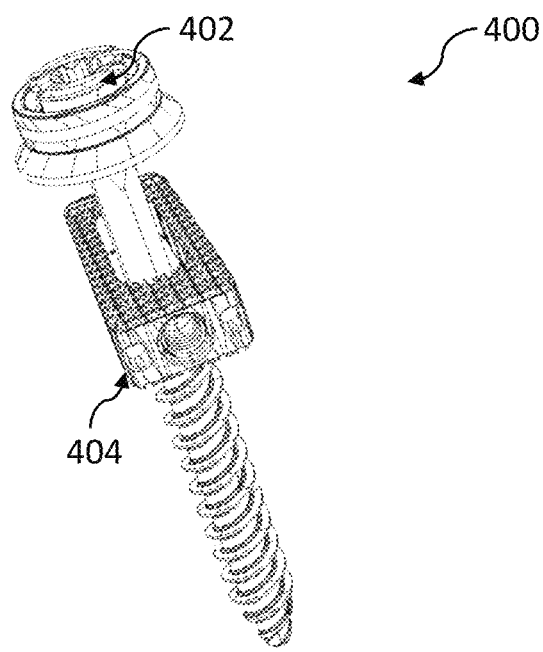
Figure 4B:
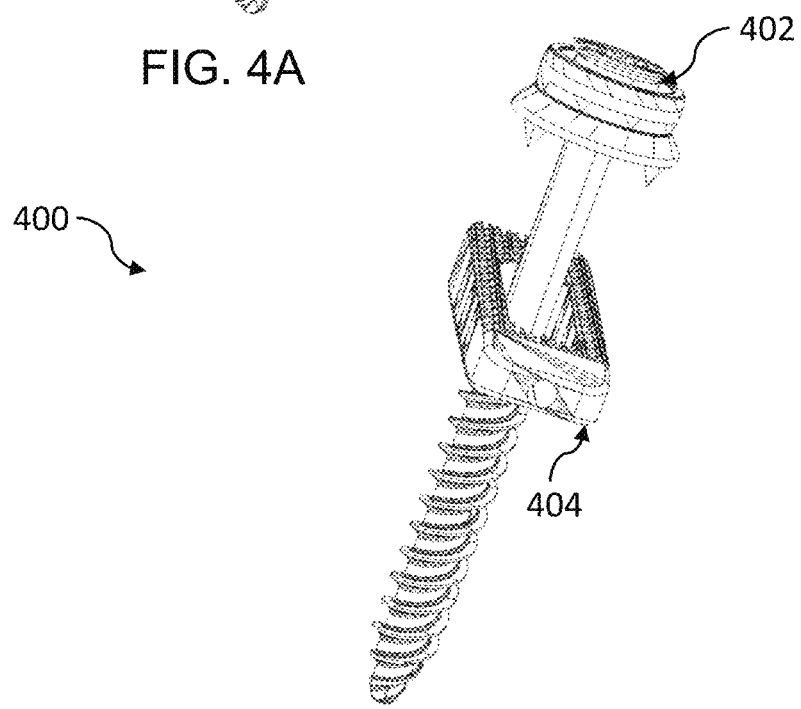
Figure 4G:
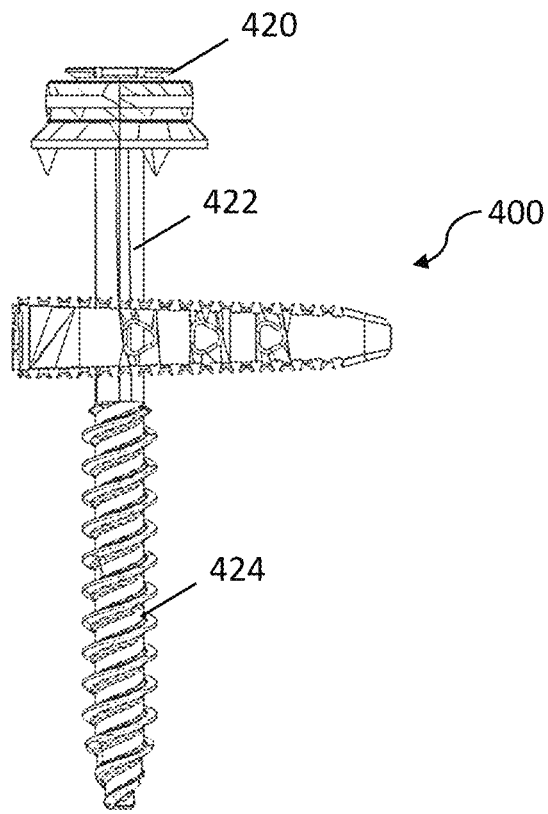
Figure 4H:
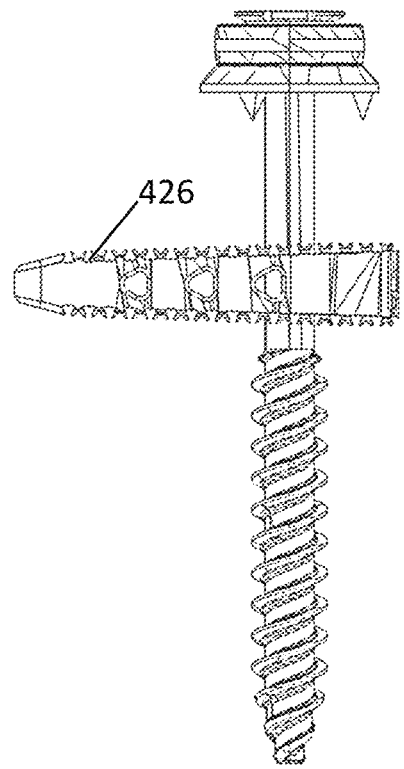
Figure 5A:
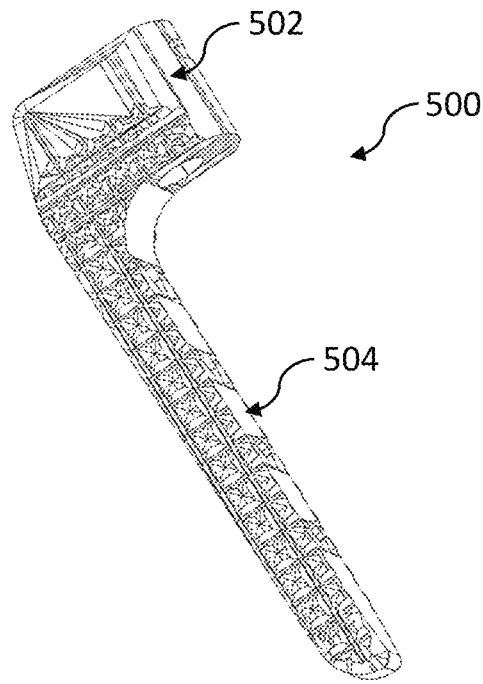
FIGS. 5A-5H depict various views of one embodiment of an L-shaped wedging cage.
Figure 5B:
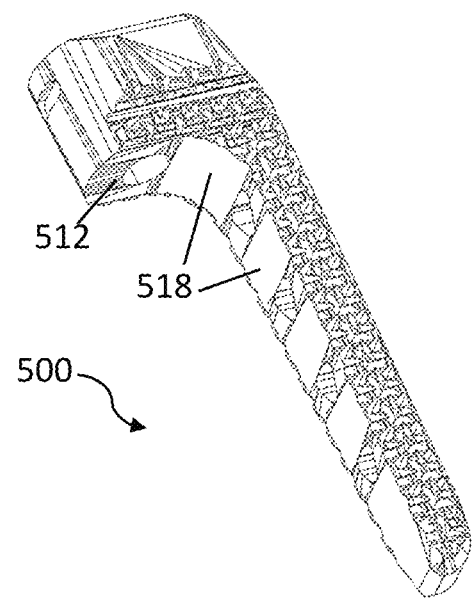
Figure 5C:
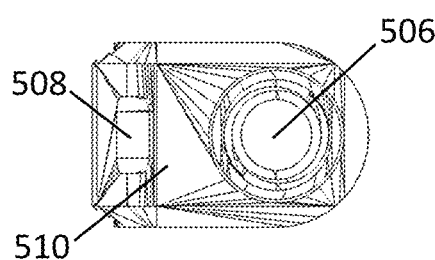
Figure 5D:
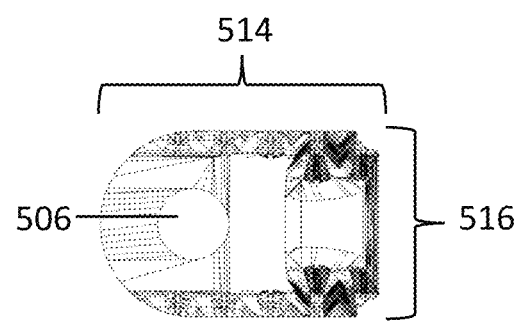
Figures 5E, 5F:
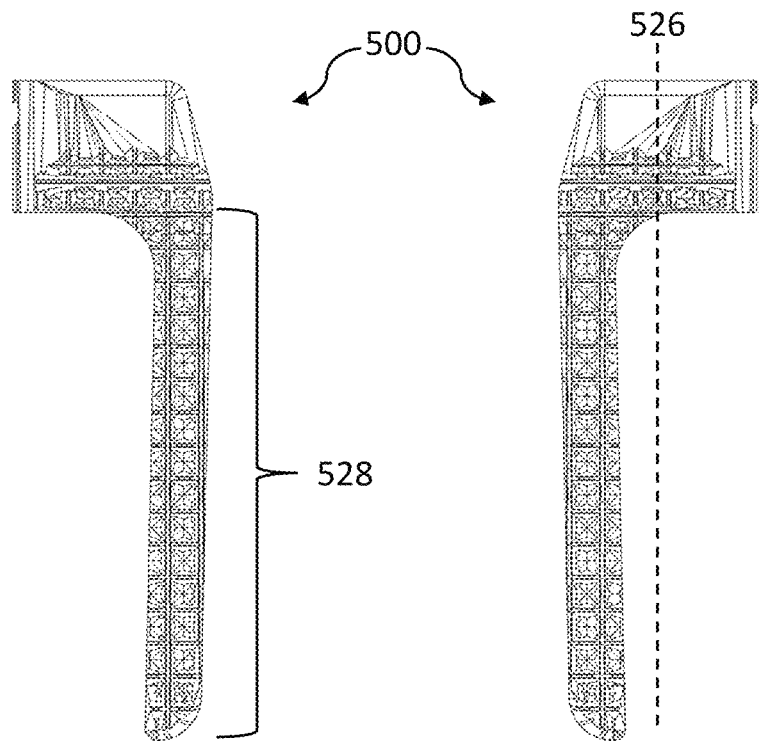
Figures 5G, 5H:
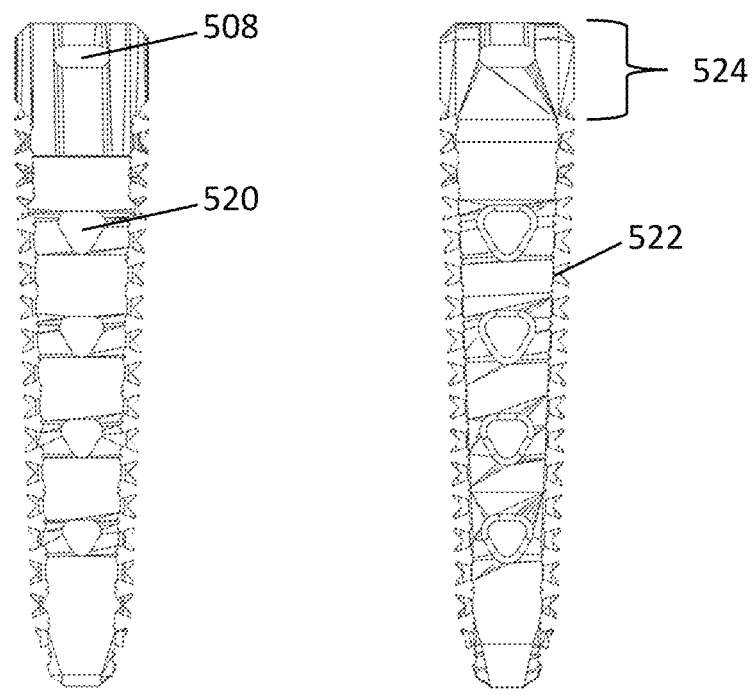
Figure 6A:
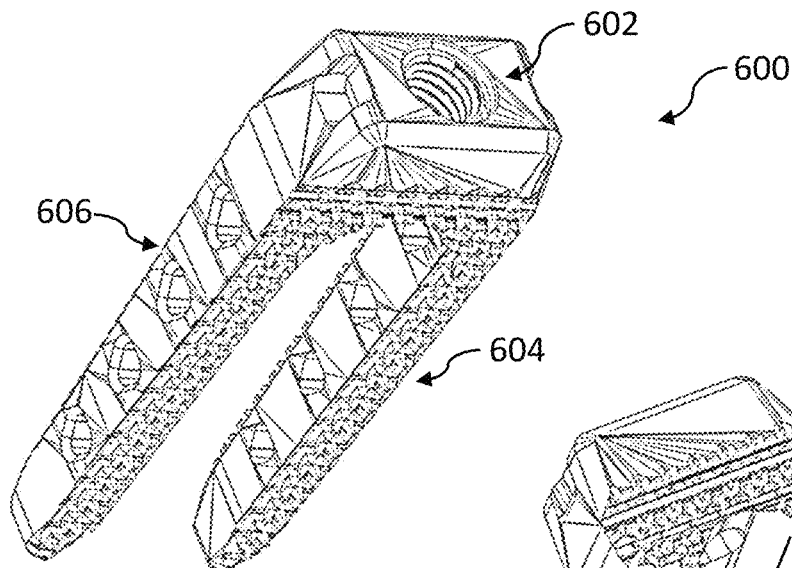
FIGS. 6A-6H depict various views of one embodiment of a U-shaped wedging cage.
Figure 6B:
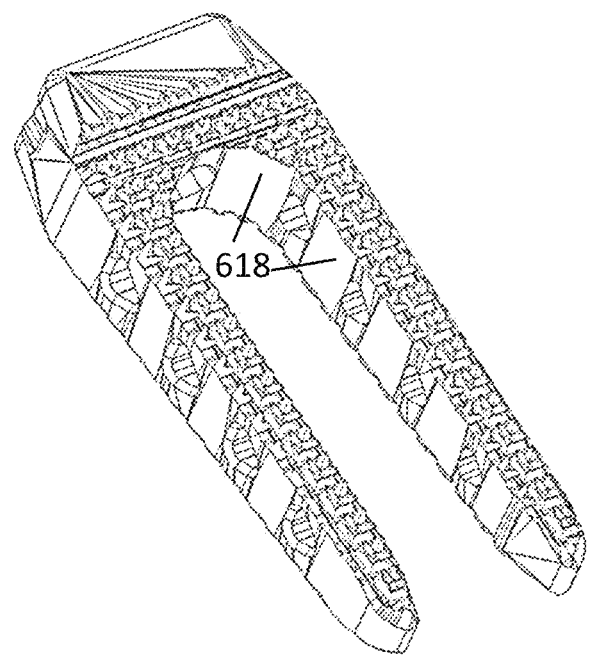
Figure 6C:
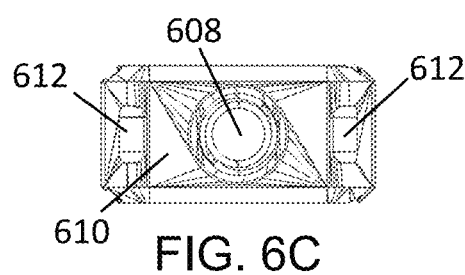
Figure 6D:
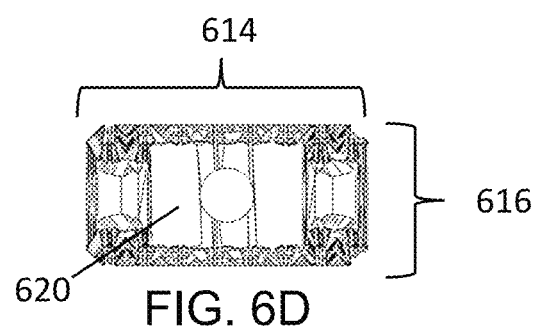
Figures 6E, 6F:
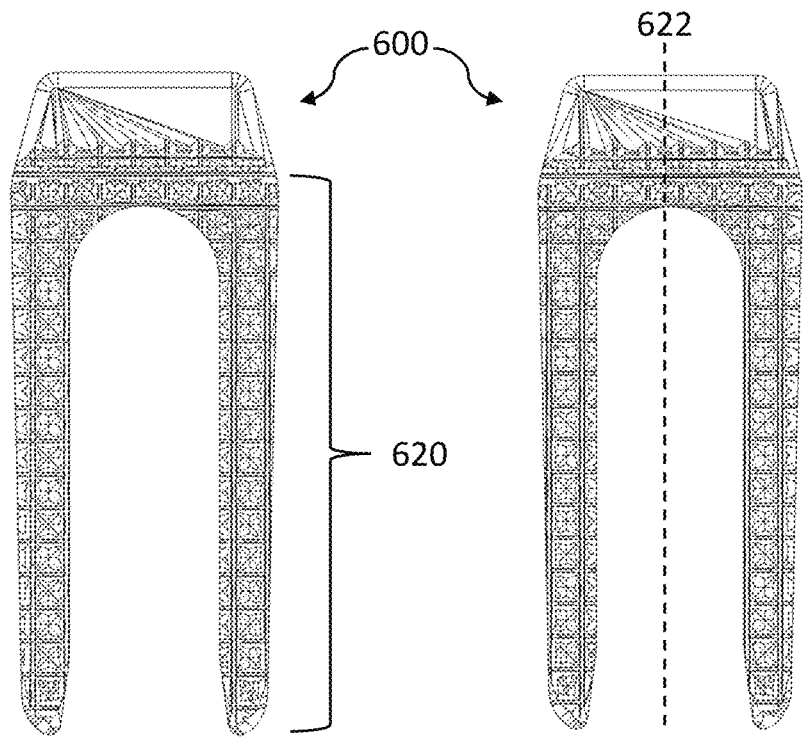
Figures 6G, 6H:
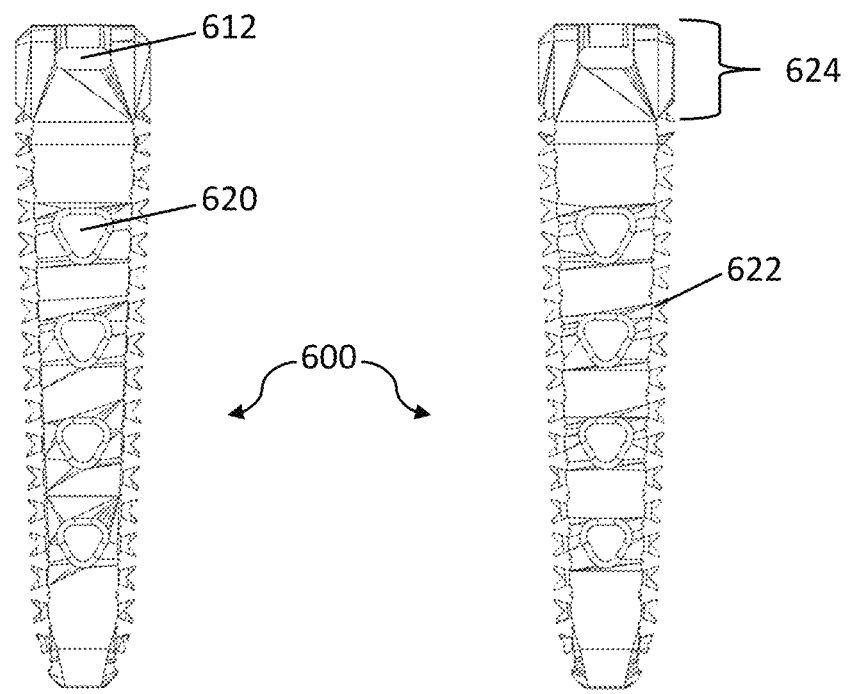

FIGS. 1A-1B illustrates one embodiment of the pelvic bones 100, namely the sacroiliac joint 106. The sacroiliac joint (SI) 106, often referred to as the "SI joint" is the space located between the sacrum bone 102 and the ilium 104. There are two SI joints 106—one on either side of the sacrum 102. The sacrum 102 locks in between the two ilia 104 (or innominates) by acting as a wedge. The top of the sacrum 102 is wider than the bottom, which enables a snug fit between the bones at that level, providing a "wedge-like" shape. The sacrum 102 and the ilium 104 are further held in place by ligaments 110, which these ligaments 110 help the sacrum support the weight of the spine and head. The space at the top of the sacrum 102 and the ilium 104 is the articular cavity 108. The articular cavity 108 allows particular SI joint implants to be inserted after the smooth articular cartilage is removed.

SI Joint Fixation Systems

FIGS. 2A-2H depict various views of one embodiment of an L-shaped wedging cage system 200. The L-shaped wedging cage system 200 comprises a wedging cage 204 and a fixation screw 202. The wedging cage 204 comprises a base 208 and at least one longitudinal member 210. The base 208 including a threaded bore 206, a top surface 212 and a bottom surface 214, the threaded bore 206 extending from a top surface 212 through the bottom surface 214. The at least one longitudinal member 210 extending from the base 208 and/or the bottom surface 214 of the base 208. The at least one longitudinal member 210 extending perpendicularly or substantially perpendicular from the base 208, the substantially perpendicular includes 0.25 degrees to 10 degrees from neutral. The at least one longitudinal member 210 including at least one bone contacting surface 216, a least a portion of the at least one bone contacting surface 216 having a smooth surface or a textured surface, the textured surface comprises grit blasting, acid etching, laser texturing, wave structures, pyramidal structures, reverse pyramidal structures and/or any combination thereof. The SI joint fixation system may further comprise a fixation screw 202, the fixation screw 202 comprises a head 218, a shaft 220 and a thread 222. The fixation screw 202 may further comprise a collar. At least a portion of the fixation screw 202 contacts or mates to a portion of the bottom surface 214 of the base 208 and at least a portion of the at least one longitudinal member 210. At least a portion of the at least one longitudinal member 210 may be positioned adjacent to a circumference of the threaded bore 206 and/or the at least one longitudinal member may be positioned offset from the threaded bore 206 to provide for the "L-shape" wedging cage.

FIGS. 3A-3H depict various views of one embodiment of a U-shaped wedging cage system 300. The SI joint fixation system 300 comprises a U-shaped wedging cage 304 and a fixation screw 302. The U-shaped wedging cage 304 comprises a base 308, a first longitudinal member 310 and a second longitudinal member 312. The base 308 including a threaded bore 306, a top surface 316 and a bottom surface 314, the threaded bore 306 extending from a top surface 316 through the bottom surface 314. The first longitudinal member 310 and the second longitudinal member 312 spaced apart and extending from the bottom surface 314 of the base 308. The first 310 and/or second 312 longitudinal member extending perpendicularly or substantially perpendicular from the base, the substantially perpendicular includes 0.25 degrees to 10 degrees from neutral. The first 310 and/or second 312 longitudinal member including at least a portion of the at least one bone contacting surface 318 have a smooth surface or a textured surface, the textured surface comprises grit blasting, acid etching, laser texturing, wave structures, pyramidal structures, reverse pyramidal structures and/or any combination thereof. The SI joint fixation system 300 may further comprise a fixation screw 302, the fixation screw 302 comprises a head 320, a shaft 322 and a thread 324. The fixation screw 302 may further comprise a collar. At least a portion of the fixation screw 302 contacts or mates to a portion of the bottom surface 314 of the base 308 and at least a portion of the first longitudinal member 310 and at least a portion of the second longitudinal member 312. The spaced apart or the spacing between the first longitudinal member 310 and the second longitudinal member 312 is sized and configured to receive a portion of the fixation screw 302 and/or sized and configured to receive the shaft 322 of the fixation screw 302 to provide the "U-shape" wedging cage.

FIGS. 4A-4H depict various views of one embodiment of an O-shaped wedging cage system 400. The wedging cage system 400 comprises a wedging cage 404 and a fixation screw 402. The wedging cage 404 comprises a first base 408, a second base 418, a first longitudinal member 410 and a second longitudinal member 412. The first base 408 including a threaded bore 406, a top surface 416 and a bottom surface 414, the threaded bore 406 extending from a top surface 416 through the bottom surface 414. The second base 418 including a through-hole 428, the through-hole 428 of the second base 418 is aligned with and/or concentrically aligned with the threaded bore 406 of the first base 408. The first longitudinal member 410 and the second longitudinal member 412 spaced apart and extending between the first base 408 and the second base 418. The first 410 and/or second longitudinal member 412 extending perpendicularly or substantially perpendicular from the first base 416 and/or the second base 418, the substantially perpendicular includes 0.25 degrees to 10 degrees from neutral. The first 410 and/or second longitudinal member 412 including at least a portion of the at least one bone contacting surface 426 have a smooth surface or a textured surface, the textured surface comprises grit blasting, acid etching, laser texturing, wave structures, pyramidal structures, reverse pyramidal structures and/or any combination thereof. The SI joint fixation system 400 may further comprise a fixation screw 402, the fixation screw comprises a head 420, a shaft 422 and a thread 424. The fixation screw 402 may further comprise a collar. At least a portion of the fixation screw 402 contacts or mates to a portion of the bottom surface 414 of the first base 408 and at least a portion of the first longitudinal member 410 and at least a portion of the second longitudinal member 412. The spaced apart or the spacing between the first longitudinal member 410 and the second longitudinal member 412 is sized and configured to receive a portion of the fixation screw 402 and/or sized and configured to receive the shaft 422 of the fixation screw 402 to provide the "O-shape" wedging cage.

Alternatively, the O-shaped wedging cage system 400 may comprise a body. The body have a first end, a second end, and an aperture that is disposed between the first end and a second end. The aperture is sized and configured to receive the fixation screw 402 and/or the aperture is sized and configured to receive the shaft 422 of the fixation screw 402. The aperture comprises an oval shape or circular shape. The first end of the body having a first bore and/or the second end of the body having a second bore. The first bore and the second bore concentrically aligned and/or axially aligned. The first bore and/or the second bore may comprise internal threads.

FIGS. 5A-5H depict various views of one embodiment of an L-shaped wedging cage 500. The L-shaped wedging cage system comprises a wedging cage 500. The wedging cage 500 comprises a base 502 and at least one longitudinal member 504. The base 502 including a threaded bore 506, at least one tool opening 508, a top surface 510 and a bottom surface 512, the threaded bore 506 extending from a top surface 510 through the bottom surface 512. The tool opening 508 is sized and configured to receive a portion of the insertion tool (not shown). The base 502 comprising a shape, the shape including an oval, square, rectangle, rounded square, rounded rectangle, and/or any combination thereof. The base 502 having a length 514, a width 516 and a depth 522. At least a portion of the base 502 having a smooth surface or a textured surface, the textured surface comprises grit blasting, acid etching, laser texturing, wave structures, pyramidal structures, reverse pyramidal structures and/or any combination thereof.

Figure 28A:
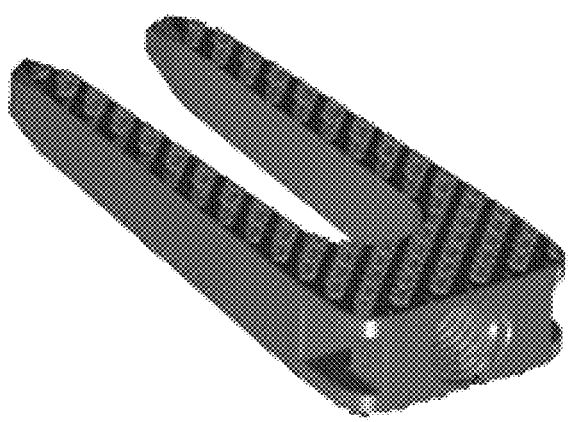
FIGS. 28A-28C depict isometric views of different embodiments of wedging cages openings.
Figure 28B:
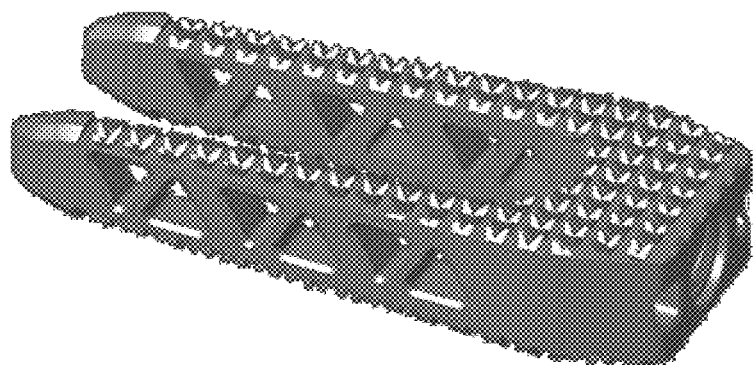
Figure 28C:
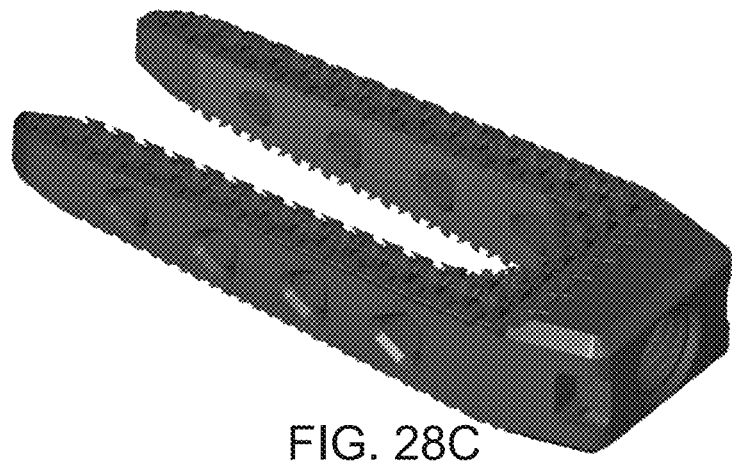

The at least one longitudinal member 510 extending from the base 502 and/or the bottom surface 512 of the base 502. The at least one longitudinal member 504 extending perpendicularly (90 degrees) or substantially perpendicular from the base 502, the substantially perpendicular includes 0.25 degrees to 10 degrees from neutral or a wedging cage axis 526. The at least one longitudinal member 504 including at least one bone contacting surface 522, a least a portion of the at least one bone contacting surface 522 having a smooth surface or a textured surface, the textured surface comprises grit blasting, acid etching, laser texturing, wave structures, pyramidal structures, reverse pyramidal structures and/or any combination thereof. the smooth or textured surface of the base 502 may be the same or different than the smooth or textured surface of the at least one longitudinal member 504. At least a portion of the at least one longitudinal member 504 may be positioned adjacent to a circumference of the threaded bore 506 and/or the at least one longitudinal member may be positioned offset from the threaded bore 506 to provide for the "L-shape" wedging cage. The at least one longitudinal member may comprise a plurality of openings 520, the plurality of openings being used to promote bone in growth and/or outgrowth. The plurality of openings 520 are spaced apart along a length 528 of the at least one longitudinal member 504. The at least one longitudinal member 504 may comprise a tapered shape. The plurality of openings 520 may comprise different shapes, the shapes include a circle, an oval, a regular polygon or irregular polygon as shown in FIGS. 28B-28C). FIG. 28A illustrates a longitudinal member with the lack of openings or being solid.

FIGS. 6A-6H depict various views of one embodiment of a SI joint fixation system comprising a U-shaped wedging cage 600. The U-shaped wedging cage 600 comprises a base 602, a first longitudinal member 604 and a second longitudinal member 606. The base 602 including a threaded bore 608, at least one tool opening 612, a top surface 610 and a bottom surface 620, the threaded bore 608 extending from a top surface 610 through the bottom surface 620. The first longitudinal member 604 and the second longitudinal member 606 spaced apart and extending from the bottom surface 620 of the base 602. The first 604 and/or second 606 longitudinal member extending perpendicularly or substantially perpendicular from the base 602, the substantially perpendicular includes 0.25 degrees to 10 degrees from neutral and/or the from neutral or a wedging cage axis 622. The at least one tool opening 612 is sized and configured to receive a portion of an insertion tool (not shown). The base 602 comprising a shape, the shape including an oval, square, rectangle, rounded square, rounded rectangle, and/or any combination thereof. The base 602 having a length 614, a width 616 and a depth 624. At least a portion of the base 602 having a smooth surface or a textured surface, the textured surface comprises grit blasting, acid etching, laser texturing, wave structures, pyramidal structures, reverse pyramidal structures and/or any combination thereof.

The first 604 and/or second 606 longitudinal member including at least a portion of the at least one bone contacting surface 622 have a smooth surface or a textured surface, the textured surface comprises grit blasting, acid etching, laser texturing, wave structures, pyramidal structures, reverse pyramidal structures and/or any combination thereof. The first longitudinal member 604 and/or the second longitudinal member 606 may comprise a plurality of openings 620, the plurality of openings being used to promote bone in growth and/or outgrowth. The plurality of openings 620 are spaced apart along a length 620 of the first longitudinal member 604 and/or the second longitudinal member 606. The first longitudinal member 604 and/or the second longitudinal member 606 may comprise a tapered shape. The plurality of openings 620 may comprise different shapes, the shapes include a circle, an oval, a regular polygon or irregular polygon as shown in FIGS. 28B-28C). FIG. 28A illustrates at least one longitudinal member with the lack of openings or being solid.

The SI joint fixation system may further comprise a fixation screw (not shown) or axial screw not shown), the fixation screw and/or the axial screw comprises a head, a shaft and a thread. The fixation screw may further comprise a collar. At least a portion of the fixation screw contacts or mates to a portion of the bottom surface 620 of the base 602 and at least a portion of the first longitudinal member 604 and at least a portion of the second longitudinal member 606. Alternatively, the first longitudinal member 604 and the second longitudinal member 606 comprises a fixation screw contacting surface 618. The spaced apart or the spacing between the first longitudinal member 604 and the second longitudinal member 606 is sized and configured to receive a portion of the fixation screw and/or sized and configured to receive the shaft of the fixation screw to provide the "U-shape" wedging cage. Accordingly, the SI joint fixation system may further comprise an axial screw. The axial screw is sized and configured to be inserted into the threaded bore 608, the threaded bore 608 is sized and configured to receive at least a portion of the axial screw.

FIGS. 7A-7H depict various views of one embodiment of a SI joint fixation system comprising an O-shaped wedging cage 700. The wedging cage 700 comprises a first base 702, a second base 726, a first longitudinal member 704 and a second longitudinal member 706. The first base 702 including a threaded bore 708, at least one tool opening 712, a top surface 710 and a bottom surface 728, the threaded bore 708 extending from a top surface 710 through the bottom surface 728. The second base 726 including a through-hole 720, the through-hole 720 of the second base 726 is aligned with and/or concentrically aligned with the threaded bore 708 of the first base 702 and/or aligned with the wedging cage axis 722. At least a portion of the base 702 having a smooth surface or a textured surface, the textured surface comprises grit blasting, acid etching, laser texturing, wave structures, pyramidal structures, reverse pyramidal structures and/or any combination thereof. The first base 702 and/or the second base 726 having a length 714, a width 716 and a depth 724.

The first longitudinal member 704 and the second longitudinal member 706 spaced apart and extending between the first base 702 and the second base 726. The first 704 and/or second longitudinal member 706 extending perpendicularly or substantially perpendicular from the first base 702 and/or the second base 726, the substantially perpendicular includes 0.25 degrees to 10 degrees from neutral and/or the wedging cage axis 722. The first 704 and/or second longitudinal member 706 including at least a portion of the at least one bone contacting surface 722 have a smooth surface or a textured surface, the textured surface comprises grit blasting, acid etching, laser texturing, wave structures, pyramidal structures, reverse pyramidal structures and/or any combination thereof. The first longitudinal member 704 and/or the second longitudinal member 706 may comprise a plurality of openings 720, the plurality of openings 720 being used to promote bone in growth and/or outgrowth. The plurality of openings 720 are spaced apart along a length 720 of the first longitudinal member 704 and/or the second longitudinal member 706. The first longitudinal member 704 and/or the second longitudinal member 706 may comprise a tapered shape. The plurality of openings 720 may comprise different shapes, the shapes include a circle, an oval, a regular polygon or irregular polygon as shown in FIGS. 28B-28C). FIG. 28A illustrates a longitudinal member with the lack of openings or being solid.

The SI joint fixation system may further comprise a fixation screw (not shown) or axial screw not shown), the fixation screw and/or the axial screw comprises a head, a shaft and a thread. The fixation screw may further comprise a collar. At least a portion of the fixation screw contacts or mates to a portion of the bottom surface 728 of the first base 702 and at least a portion of the first longitudinal member 704 and at least a portion of the second longitudinal member 706. Alternatively, the first longitudinal member 704 and the second longitudinal member 706 comprises a fixation screw contacting surface 718. The spaced apart or the spacing between the first longitudinal member 704 and the second longitudinal member 706 is sized and configured to receive a portion of the fixation screw and/or sized and configured to receive the shaft of the fixation screw to provide the "O-shape" wedging cage. Accordingly, the SI joint fixation system may further comprise an axial screw. The axial screw is sized and configured to be inserted into the threaded bore 708, the threaded bore 708 is sized and configured to receive at least a portion of the axial screw.

Alternatively, the O-shaped wedging cage 700 may comprise a body. The body have a first end, a second end, and an aperture that is disposed between the first end and a second end. The aperture is sized and configured to receive a portion of a fixation screw and/or the aperture is sized and configured to receive the shaft of the fixation screw. The aperture comprises an oval shape or circular shape. The first end of the body having a first bore and/or the second end of the body having a second bore. The first bore and the second bore concentrically aligned and/or axially aligned. The first bore and/or the second bore may comprise internal threads.

Figure 8:
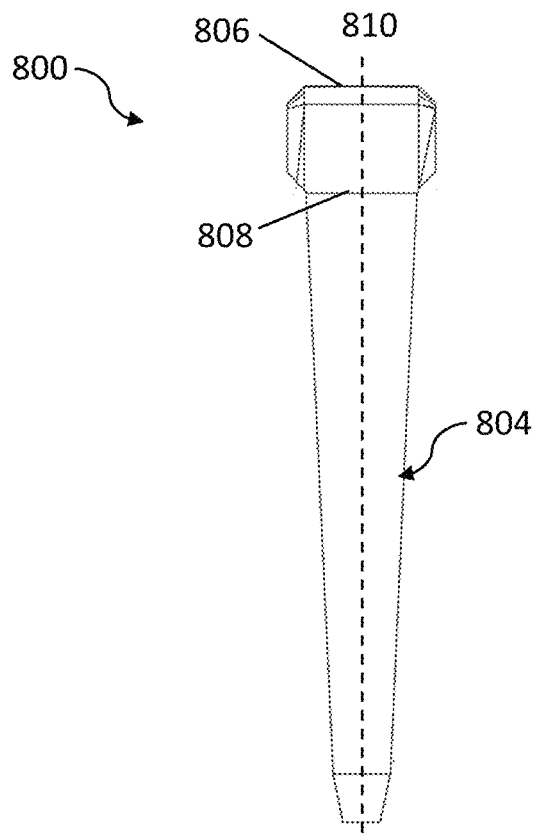
FIG. 8 depicts a side view of one embodiment of an I-shaped wedging cage.

FIG. 8 depicts a side view of one embodiment of an SI joint fixation system comprising an I-shaped wedging cage 800. The I-shaped wedging cage system comprises a wedging cage 800. The wedging cage 800 comprises a base 802 and at least one longitudinal member 804. The base 802 including a threaded bore (not shown), at least one tool opening (not shown), a top surface 806 and a bottom surface 808, the threaded bore extending from a top surface 806 through the bottom surface 808. The tool opening is sized and configured to receive a portion of the insertion tool (not shown). The base 802 comprising a shape, the shape including an oval, square, rectangle, rounded square, rounded rectangle, and/or any combination thereof. The base 802 having a length, a width and a depth. At least a portion of the base 802 having a smooth surface or a textured surface, the textured surface comprises grit blasting, acid etching, laser texturing, wave structures, pyramidal structures, reverse pyramidal structures and/or any combination thereof.

The at least one longitudinal member 804 extending from the base 802 and/or the bottom surface 80812 of the base 802. The at least one longitudinal member 804 extending perpendicularly (90 degrees) or substantially perpendicular from the base 802, the substantially perpendicular includes 0.25 degrees to 10 degrees from neutral or a wedging cage axis 810. The at least one longitudinal member 804 including at least one bone contacting surface, a least a portion of the at least one bone contacting surface having a smooth surface or a textured surface, the textured surface comprises grit blasting, acid etching, laser texturing, wave structures, pyramidal structures, reverse pyramidal structures and/or any combination thereof. the smooth or textured surface of the base 802 may be the same or different than the smooth or textured surface of the at least one longitudinal member 804. The at least one longitudinal member 804 may be positioned adjacent to a circumference of the threaded bore 506 and/or the at least one longitudinal member may be positioned offset from the threaded bore 506 to provide for the "L-shape" wedging cage. The at least one longitudinal member may comprise a plurality of openings (not shown), the plurality of openings being used to promote bone in growth and/or outgrowth. The plurality of openings are spaced apart along a length of the at least one longitudinal member 804. The at least one longitudinal member 804 may comprise a tapered shape. The plurality of openings may comprise different shapes, the shapes include a circle, an oval, a regular polygon or irregular polygon as shown in FIGS. 28B-28C). FIG. 28A illustrates a longitudinal member with the lack of openings or being solid.

Figure 9:
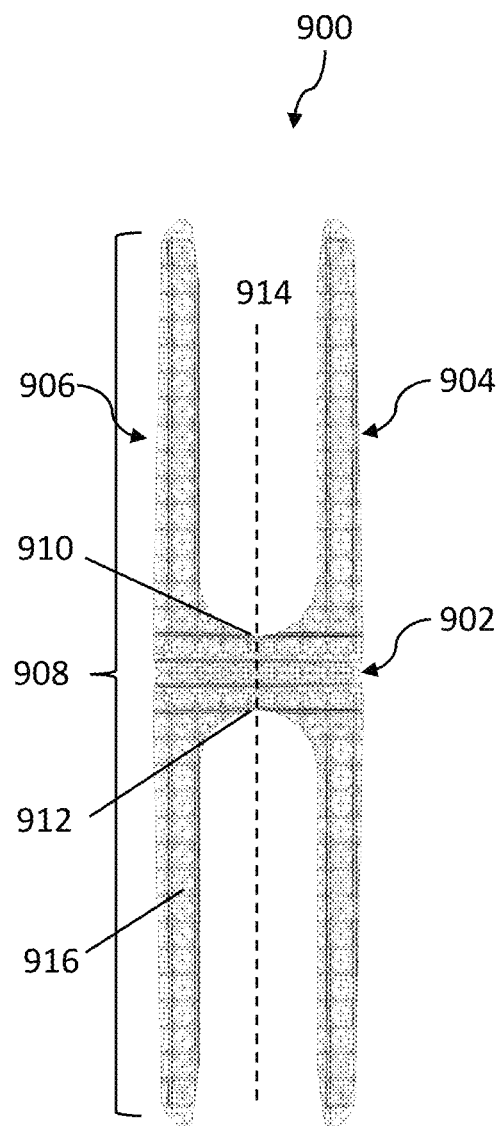
FIG. 9 depicts a side view of one embodiment of an H-shaped wedging cage.

FIG. 9 depicts a side view of one embodiment of an SI joint fixation system comprising an H-shaped wedging cage 900. The H-shaped wedging cage 900 comprises a base 902, a first longitudinal member 904 and a second longitudinal member 906. The base 902 including a threaded bore (not shown), at least one tool opening (now shown), a top surface 910 and a bottom surface 912, the threaded bore extending from a top surface 910 through the bottom surface 912. The first longitudinal member 904 and the second longitudinal member 906 spaced apart and extending from opposite sides of the base 902. The first 904 and/or second 906 longitudinal member extending perpendicularly or substantially perpendicular from the base 902, the substantially perpendicular includes 0.25 degrees to 10 degrees from neutral and/or the from neutral or a wedging cage axis 914. The at least one tool opening is sized and configured to receive a portion of an insertion tool (not shown). The base 902 comprising a shape, the shape including an oval, square, rectangle, rounded square, rounded rectangle, and/or any combination thereof. The base 902 having a length 908, a width and a depth. At least a portion of the base 902 having a smooth surface or a textured surface, the textured surface comprises grit blasting, acid etching, laser texturing, wave structures, pyramidal structures, reverse pyramidal structures and/or any combination thereof. The base 902 may extend between the first longitudinal member 904 and the second longitudinal member 906, and be positioned anywhere along the length 908 of the first longitudinal member 904 and the second longitudinal member 906.

The first 904 and/or second 906 longitudinal member including at least a portion of the at least one bone contacting surface 916 have a smooth surface or a textured surface, the textured surface comprises grit blasting, acid etching, laser texturing, wave structures, pyramidal structures, reverse pyramidal structures and/or any combination thereof. The first longitudinal member 904 and/or the second longitudinal member 906 may comprise a plurality of openings (not shown), the plurality of openings being used to promote bone in growth and/or outgrowth. The plurality of openings are spaced apart along a length 908 of the first longitudinal member 904 and/or the second longitudinal member 906. The first longitudinal member 904 and/or the second longitudinal member 906 may comprise a tapered shape. The plurality of openings may comprise different shapes, the shapes include a circle, an oval, a regular polygon or irregular polygon as shown in FIGS. 28B-28C). FIG. 28A illustrates a longitudinal member with the lack of openings or being solid.

The SI joint fixation system may further comprise a fixation screw (not shown) or axial screw not shown). The fixation screw and/or the axial screw comprises a head, a shaft and a thread. The fixation screw may further comprise a collar. The fixation screw is intended to be positioned or deployed perpendicular to the axis 914 of the wedging cage. At least a portion of the fixation screw contacts or mates to a portion of the bottom surface 912 of the base 902 and at least a portion of the first longitudinal member 904 and at least a portion of the second longitudinal member 906. Alternatively, the first longitudinal member 904 and the second longitudinal member 906 comprises a fixation screw contacting surface. The spaced apart or the spacing between the first longitudinal member 904 and the second longitudinal member 906 is sized and configured to receive a portion of the fixation screw and/or sized and configured to receive the shaft of the fixation screw to provide the "H-shape" wedging cage. Alternatively, the wedging cage 900 spaced apart or spacing between the first longitudinal member 904 and the second longitudinal member 906 is sized and configured to receive a portion of a two or more fixation screws. Each of the two or more fixation screws may be positioned adjacent to or contacting the top surface 910 of the base 902 and/or the bottom surface 912 of the base 902. Accordingly, the SI joint fixation system may further comprise an axial screw. The axial screw is sized and configured to be inserted into the threaded bore, the threaded bore is sized and configured to receive at least a portion of the axial screw. The axial screw is intended to be positioned or deployed parallel to the axis 914 of the wedging cage 900.

Figure 10A:
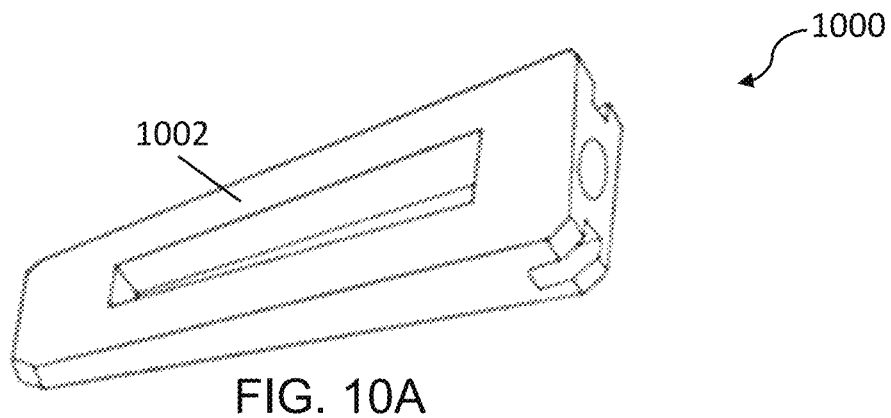
FIGS. 10A-10C depict various isometric views of different embodiments of surface textures.
Figure 10B:
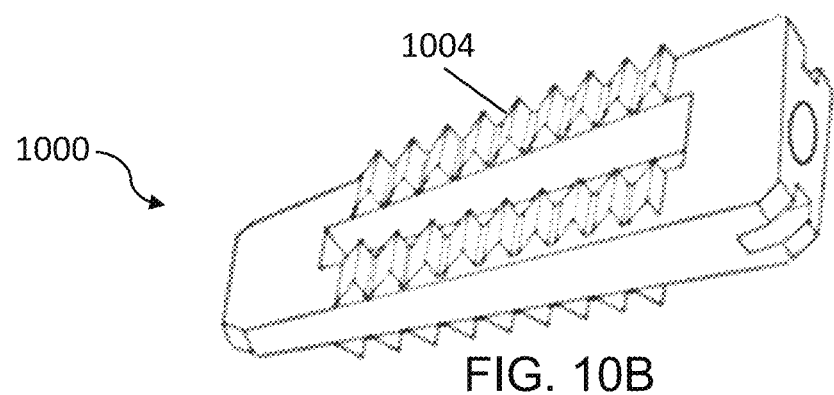
Figure 10C:
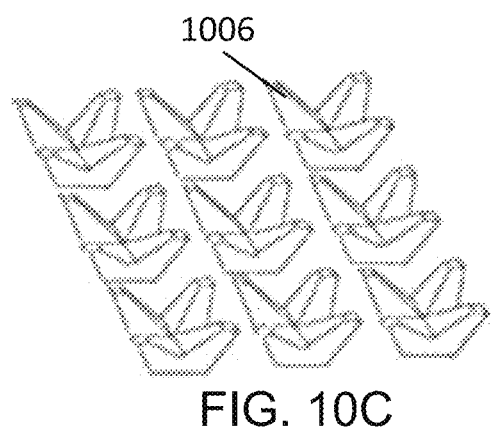
Figure 11A:
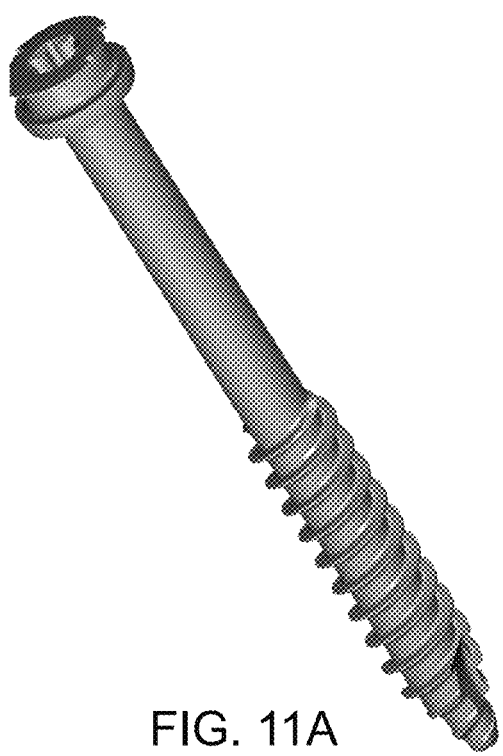
FIGS. 11A-11E depict various views of one embodiment of a screw.
Figure 11B:
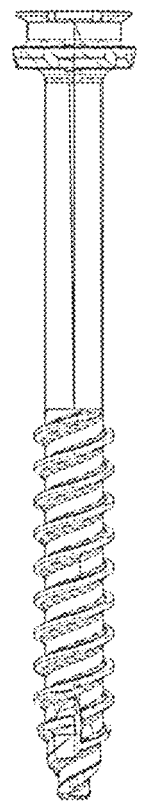
Figure 11C:
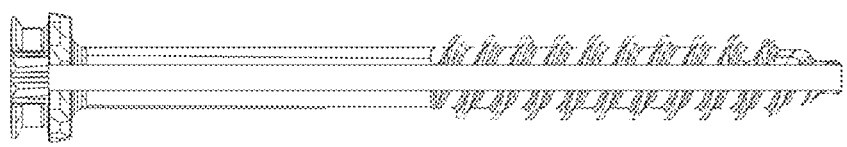
Figure 11D:
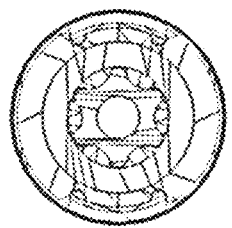
Figure 11E:
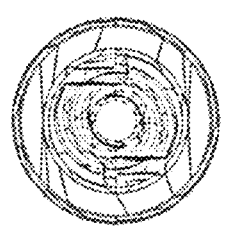
Figure 12A:
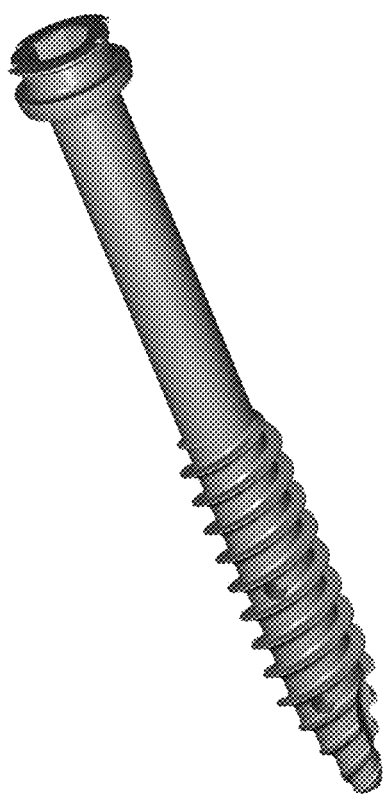
FIGS. 12A-12E depict various views of an alternate embodiment of a screw.
Figure 12B:
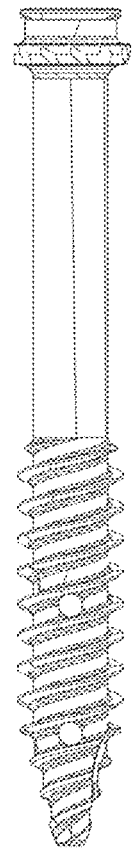
Figure 12C:
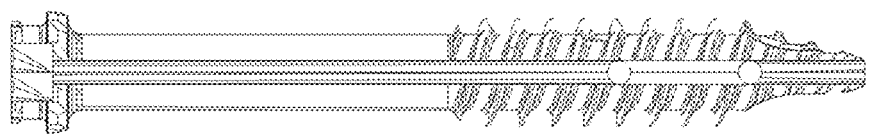
Figure 12D:
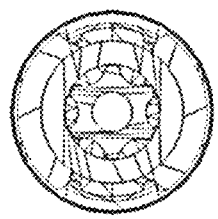
Figure 12E:
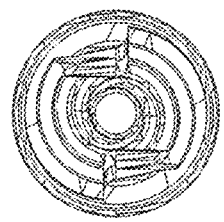
Figure 14A:
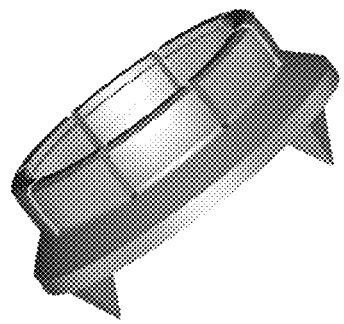
FIGS. 14A-14E depict various views of one embodiment of a collar.
Figure 14B:
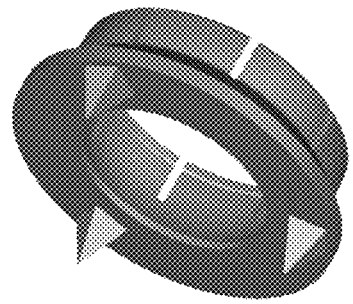
Figure 14C:
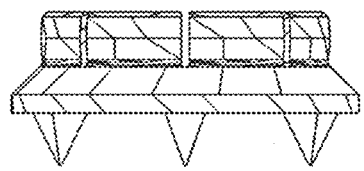
Figure 14D:
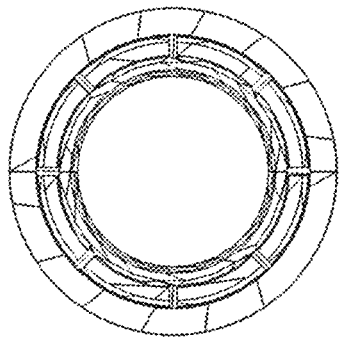
Figure 14E:
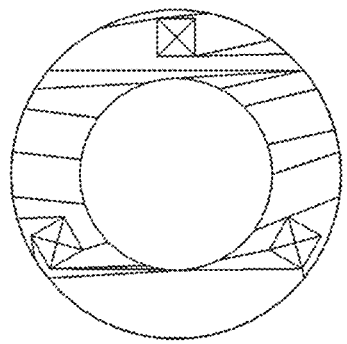

FIG. 10A-10C depict various isometric views of different embodiments of surface textures disposed on wedging cages 1000. Varying and/or enhancing the wedging cage surfaces may accelerate bone anchorage to the implants thereby providing optimal support for stability, osseointegration, and reduced complications. At least a portion of one bone contacting surface of the wedging cages 1000 described above may comprise a smooth surface and/or textured surfaces or modified surface. The textured surface comprises grit blasting, acid etching, laser texturing, plasma spraying, electropolishing, anodic oxidation, hydroxylapatite (HA), calcium phosphate (CaP), wave structures 1004, pyramidal structures, reverse pyramidal structures 1006, undulations, and/or any combination thereof. Alternatively, at least a portion of the one bone contacting surface of the wedging cages 1000 described above may comprise an osseointegration coating. The osseointegration coating comprises peptide coating, collagen coating, strontium titanate (SrTiO3) coating, protein coatings, PEEK, and/or any combination thereof. The wedging cages 1000 may comprise an "H-shaped" wedging cage, "I-shaped" wedging cage, and "L-shaped" wedging cage, a "U-shaped" wedging cage and/or an "O-shaped" wedging cage.

FIGS. 11A-11E, FIGS. 12A-12E and FIGS. 13A-13E depict various views of an alternative embodiment of fixation screws. The fixation screws comprise a head, shaft and a thread. The fixation screws may comprise self-tapping screws. At least a portion of the screw length may have a fine or coarse self-tapping thread. The length of threaded portion of the screw is suitably from 10 to 50 mm. It is generally suitable to manufacture screws in various sizes such that the length of the said threaded portion varies so different sized screws can be chosen for any particular application. The head may comprise a channel, the channel may be disposed on the circumference of the head of the screw. The channel may be sized and configured to receive a portion of a collar. The head may further comprise a driving tool recess, the driving tool recess may comprise a shape that is sized and configured to receive a slotted driver, a cruciform driver, external polygon driver, internal polygon driver, hexalobular driver, three-pointed driver, special driver and/or any combination thereof. The screw shaft and thread may have a diameter. The shaft diameter may be smaller and/or greater than the thread. The fixation screws may further comprise a collar as shown in FIGS. 14A-14E. The collar may be self-leveling to at least one surface of the sacrum and/or ilium.

Figure 15A:
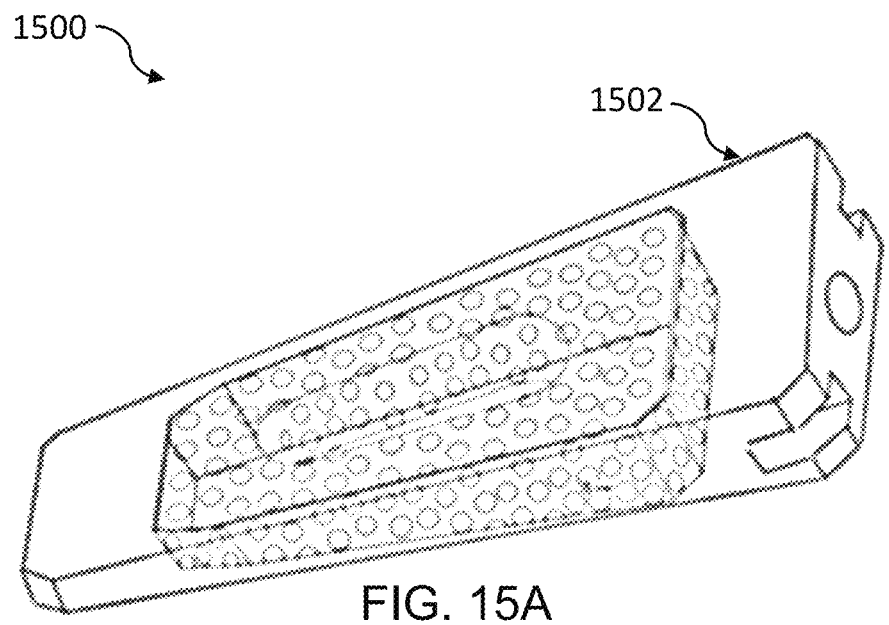
FIGS. 15A-15D depict isometric views of different embodiments of a shell wedging cage system.
Figure 15B:
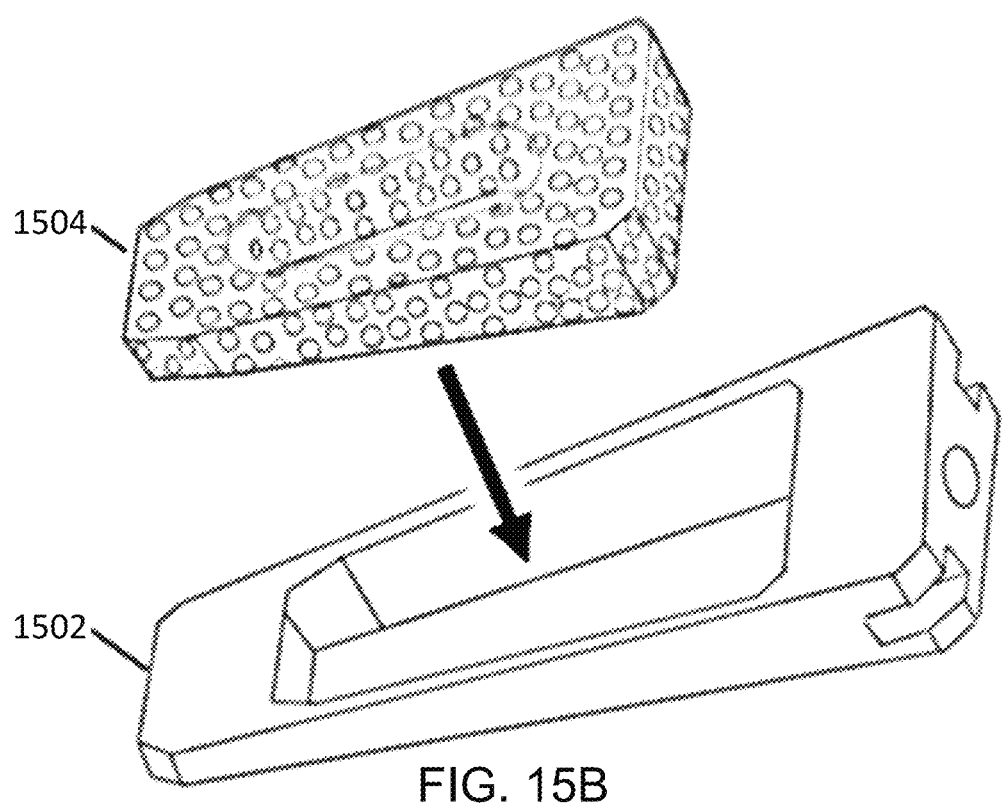
Figure 15C:
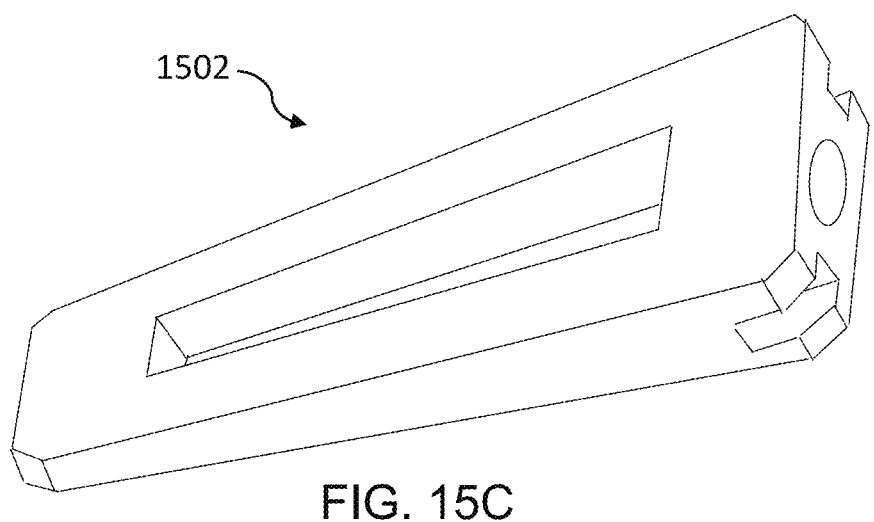
Figure 15D:
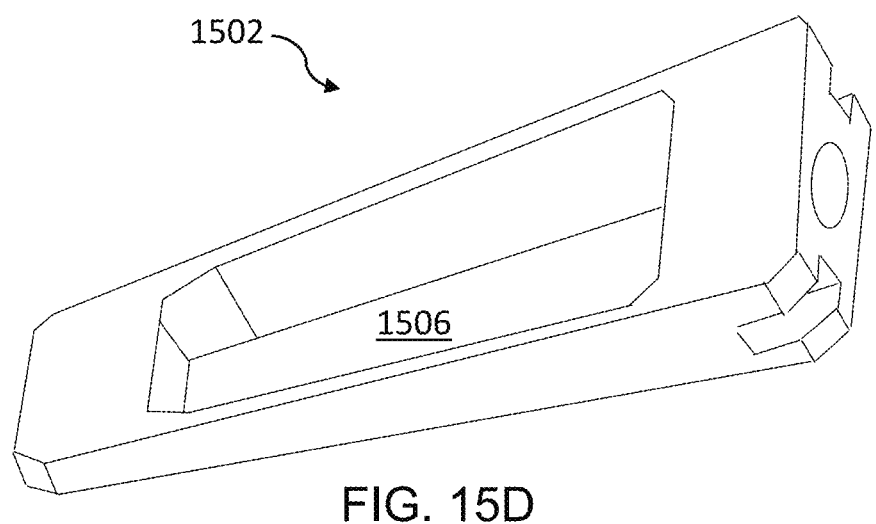
Figures 16A, 16B:
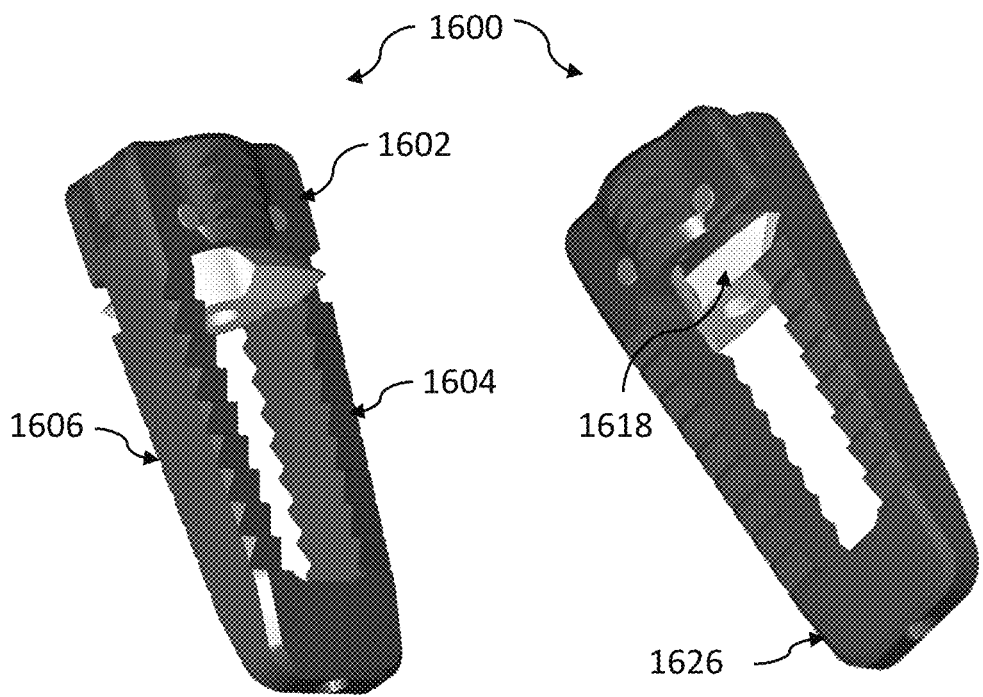
FIGS. 16A-16G depict various views of one embodiment of an anchored wedging cage system.
Figures 16C, 16D:
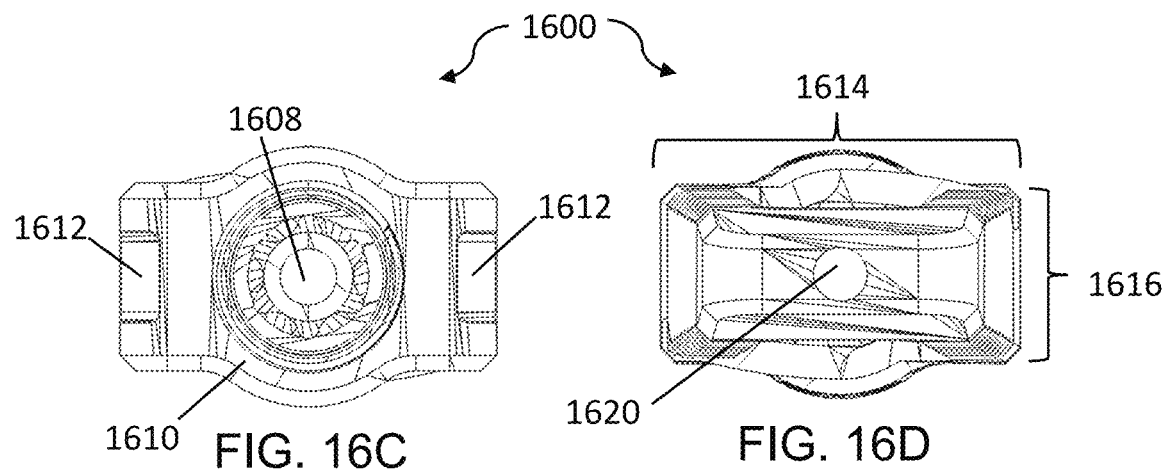
Figures 16E, 16F:
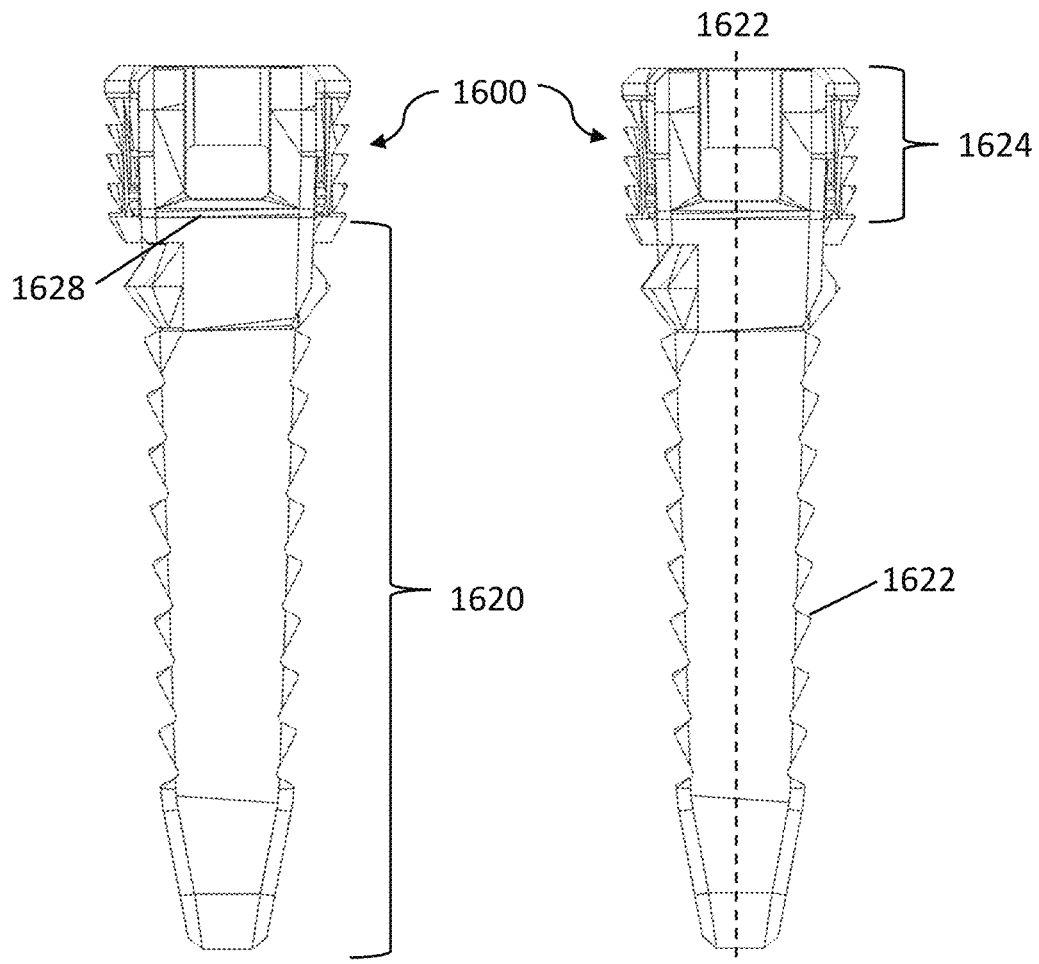
Figure 16G:
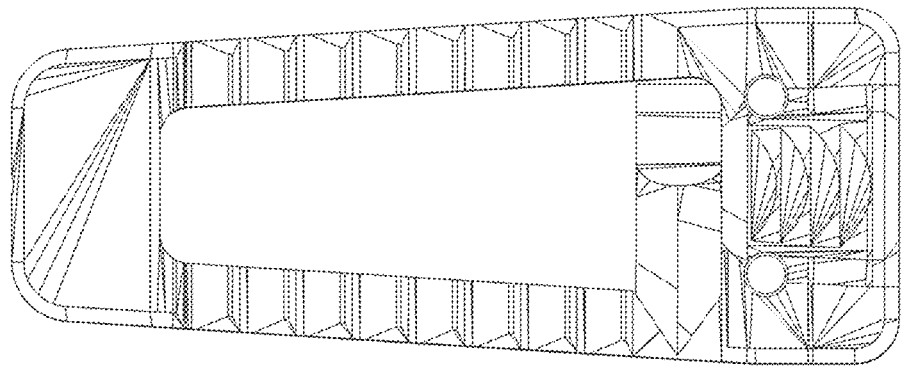
Figures 17A, 17B:
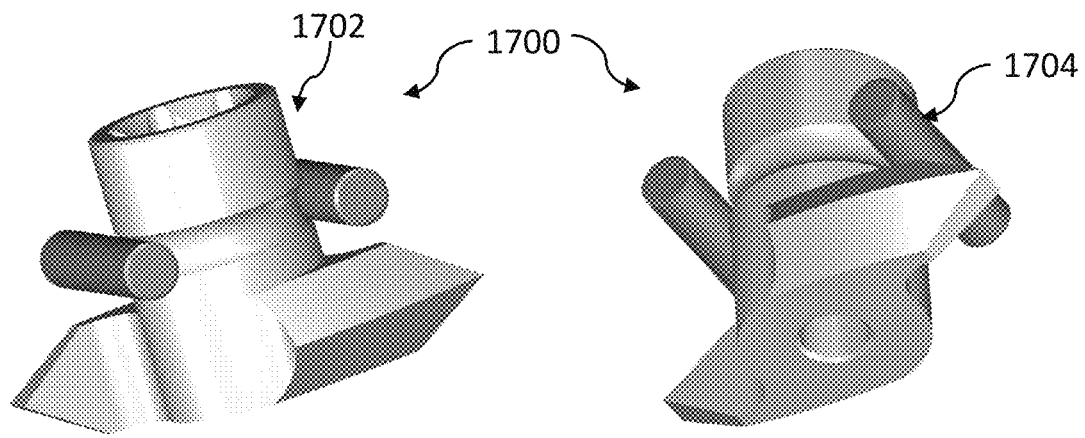
FIGS. 17A-17E depict various views of one embodiment of an anchor assembly.
Figure 17C:
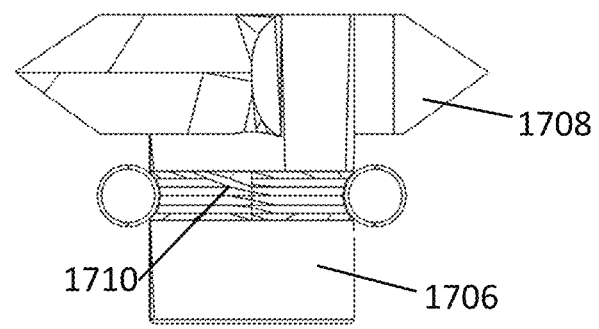
Figures 17D, 17E:
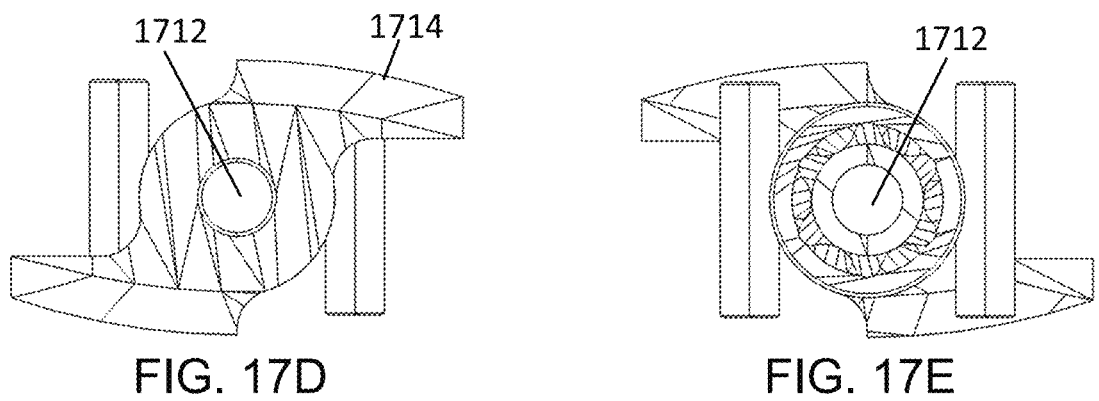

FIGS. 15A-15D depict isometric views of different embodiments on SI joint fixation system comprise a shell wedging cage 1500. The shell wedging cage 1500 comprises a wedging cage 1502 and a bone growth block 1504. The wedging cage 1500 comprises an "O-shaped" wedging cage. The "O-shaped" wedging cage comprises a body, the body including an aperture 1506. The aperture 1506 is sized and configured to receive the bone growth block 1504. The aperture may be frustum shaped allowing the bone growth block 1504 to be wedged into the aperture. The aperture 1506 may include different widths and lengths as shown in FIG. 15C-15D.

In another embodiment, the wedging cage 1502 may also comprise an "H-shaped" wedging cage, an "I-shaped" wedging cage, a "U-shaped" wedging cage, and an "L-shaped" wedging cage, and/or any combination thereof. At least a portion of the base, the at least one longitudinal member, the first longitudinal member, and/or the second longitudinal member may comprise a channel (not shown), the channel is sized and configured to receive a portion of the bone growth block 1504. Alternatively, at least a portion of the base, the at least one longitudinal member, the first longitudinal member, and/or the second longitudinal member may comprise a ledge (not shown), the ledge extends perpendicular from a surface of the base, the at least one longitudinal member, the first longitudinal member, and/or the second longitudinal member. The ledge having a top surface that contacts or mates with a portion of the bone growth block 1504.

FIGS. 16A-16G depict various views of one embodiment of an SI joint fixation system comprising an anchored wedging cage 1600. The anchored wedging cage comprises a wedging cage and an anchor assembly 1618. The wedging cage comprises a first base 1602, a second base 1626, a first longitudinal member 1604 and a second longitudinal member 1606. The first base 1602 including a bore 1608, at least one tool opening 1612, a top surface 1610 and a bottom surface, the bore 1608 extending from a top surface 1610 through the bottom surface 1628. The second base 1626 including a second bore or through-hole 1620, the through-hole 1620 of the second base 1626 is aligned with and/or concentrically aligned with the bore 1608 of the first base 1602 and/or aligned with the wedging cage axis 1622. The first base 1602 and/or the second base 1626 including a width 1616, a depth 1624, and a length 1624. At least a portion of the base 1602 having a smooth surface or a textured surface, the textured surface comprises grit blasting, acid etching, laser texturing, wave structures, pyramidal structures, reverse pyramidal structures and/or any combination thereof. Alternatively, the wedging cage may comprise an I-shaped, L-shaped, H-shaped, O-shaped, U-shaped wedging cage and/or any combination thereof.

The first longitudinal member 1604 and the second longitudinal member 1606 spaced apart and extending between the first base 1602 and the second base 1626. The first 1604 and/or second longitudinal member 1606 extending perpendicularly or substantially perpendicular from the first base 1602 and/or the second base 1626, the substantially perpendicular includes 0.25 degrees to 10 degrees from neutral and/or the wedging cage axis 1622. The first 1604 and/or second longitudinal member 706 including at least a portion of the at least one bone contacting surface 1622 have a smooth surface or a textured surface, the textured surface comprises grit blasting, acid etching, laser texturing, wave structures, pyramidal structures, reverse pyramidal structures and/or any combination thereof. The first longitudinal member 1604 and/or the second longitudinal member 1606 may comprise a plurality of openings, the plurality of openings being used to promote bone in growth and/or outgrowth. The plurality of openings are spaced apart along a length 1620 of the first longitudinal member 1604 and/or the second longitudinal member 1606. The first longitudinal member 1604 and/or the second longitudinal member 1606 may comprise a tapered shape. The plurality of openings may comprise different shapes, the shapes include a circle, an oval, a regular polygon or irregular polygon as shown in FIGS. 28B-28C). FIG. 28A illustrates a longitudinal member with the lack of openings or being solid.

FIGS. 17A-17E depict various views of one embodiment of an anchor assembly 1700. The anchor assembly 1700 includes an anchor body 1702 and at least two pins 1704. The anchor body 1702 comprises a shaft 1706 and at least one flute 1708. The shaft 1706 further comprising a channel 1710 and a bore 1712. The channel 1710 being disposed around a circumference of the shaft 1706. The channel being sized and configured to receive a portion of the at least two pins 1704. The bore 1608 of the first base 1602 is sized and configured to receive a portion of the anchor assembly 1700. More specifically, the bore 1608 of the first base 1602 is sized and configured to receive the shaft 1706 the anchor assembly 1700. The bore 1712 may have a driving surfaces, the driving surfaces including a shape, the shape may be sized and configured to receive different drivers, the drivers may comprise slotted driver, a cruciform driver, external polygon driver, internal polygon driver, hexalobular driver, three-pointed driver, special driver and/or any combination thereof. The at least one flute 1708 being positioned around the circumference of the shaft 1706. In one embodiment, the anchor assembly 1700 comprises a first flute and a second flute, the first and second flute being positioned on the circumference of the shaft 1706 and on opposite sides symmetrically. The flutes cut a channel or remove bone during rotation, allowing the anchor assembly to be locked into place. The at least one flute 1708, the first flute and/or the second flute comprising a cutting surface 1714.

Figure 18A:
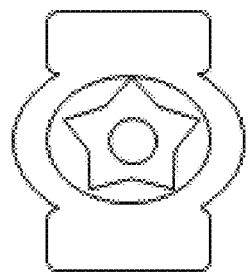
FIGS. 18A-18B depict top view of one embodiment of the locked and unlocked position of the anchored wedging cage system.
Figure 18B:
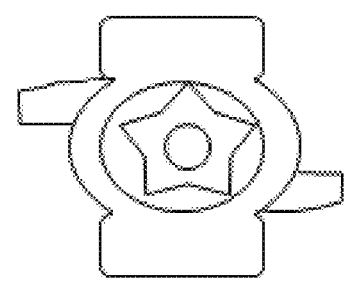
Figure 19A:
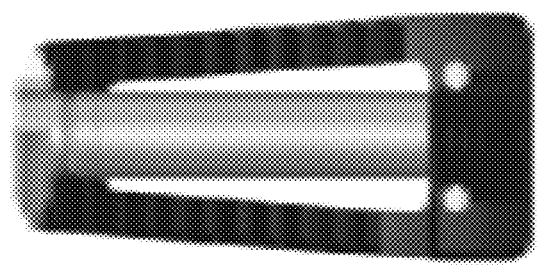
FIGS. 19A-19D depict front views of various embodiments of the axial positioning of the anchor assembly within the anchored wedging cage system.
Figure 19B:
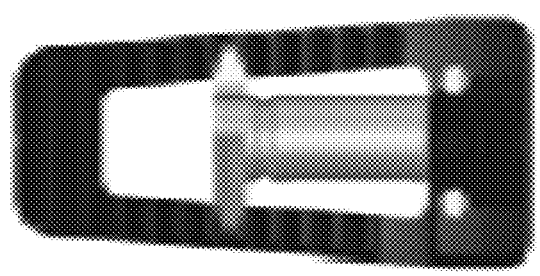
Figure 19C:
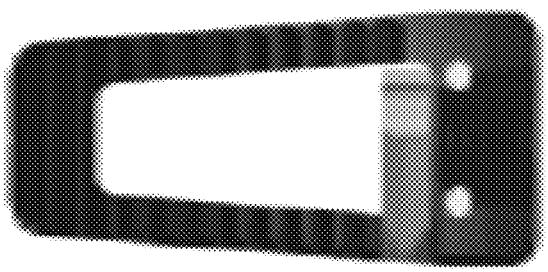
Figure 19D:
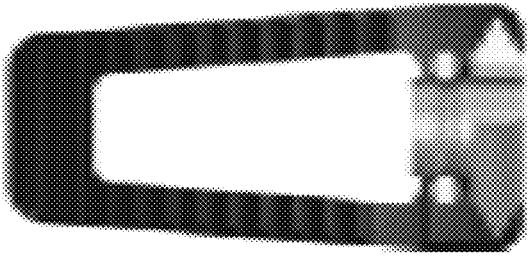

The anchor assembly is rotatable from an unlocked position to a locked position as shown in FIGS. 18A-18B. The unlocked position (see FIG. 18A) has the at least a portion of the anchor mating with a portion of the wedging cage and it allows the wedging cage to move or slide within the SI joint. The unlocked position has a low profile. The locked position (see FIG. 18B) rotates the anchor body anywhere between 1 degree to 90 degrees away from the portion of the wedging cage and allows the wedging cage to lock into place within the SI joint by removing bone material within the SI joint to provide a positive stop. The positive stop reduces slippage, migration, and loosening.

FIGS. 19A-19D depict front views of various embodiments of the axial positioning of the anchor assembly within the anchored wedging cage system. The SI joint fixation system may have anchored wedging cages 1902, 1904, 1906, 1908 with different anchoring assembly lengths. The anchoring assemblies may be easily removable to allow the surgeon to have selectivity for different anchoring lengths. The anchoring assemblies comprise an anchor body, the anchor body comprises a shaft and at least one flute. The shaft including a length, the length may vary depending on the surgeons desired length and limited joint space.

Figure 20A:
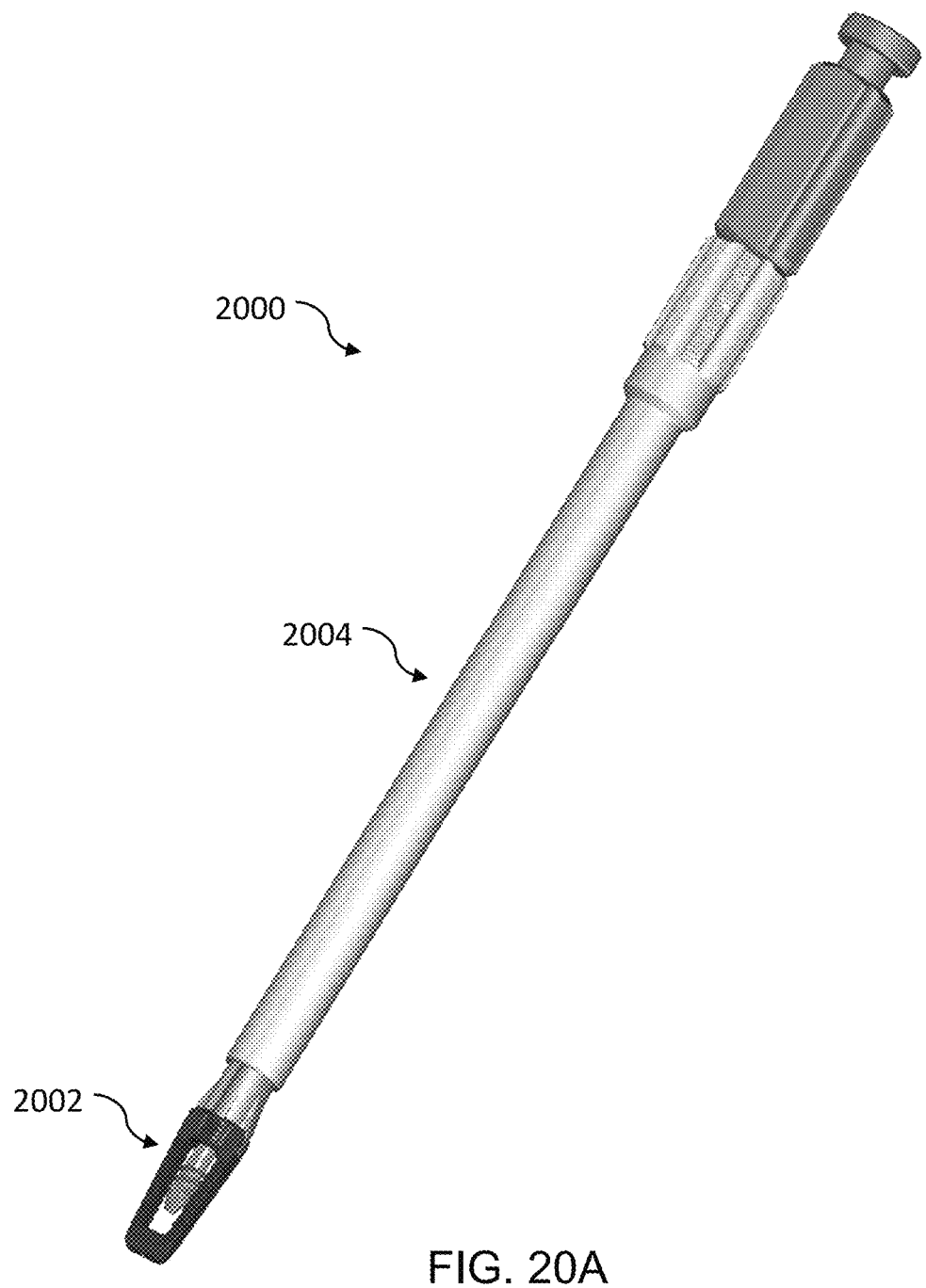
FIGS. 20A-20C depict various views of one embodiment of an axial threaded wedging cage system comprising a delivery instrument.
Figure 20B:
Figure 20C:
Figure 20D:
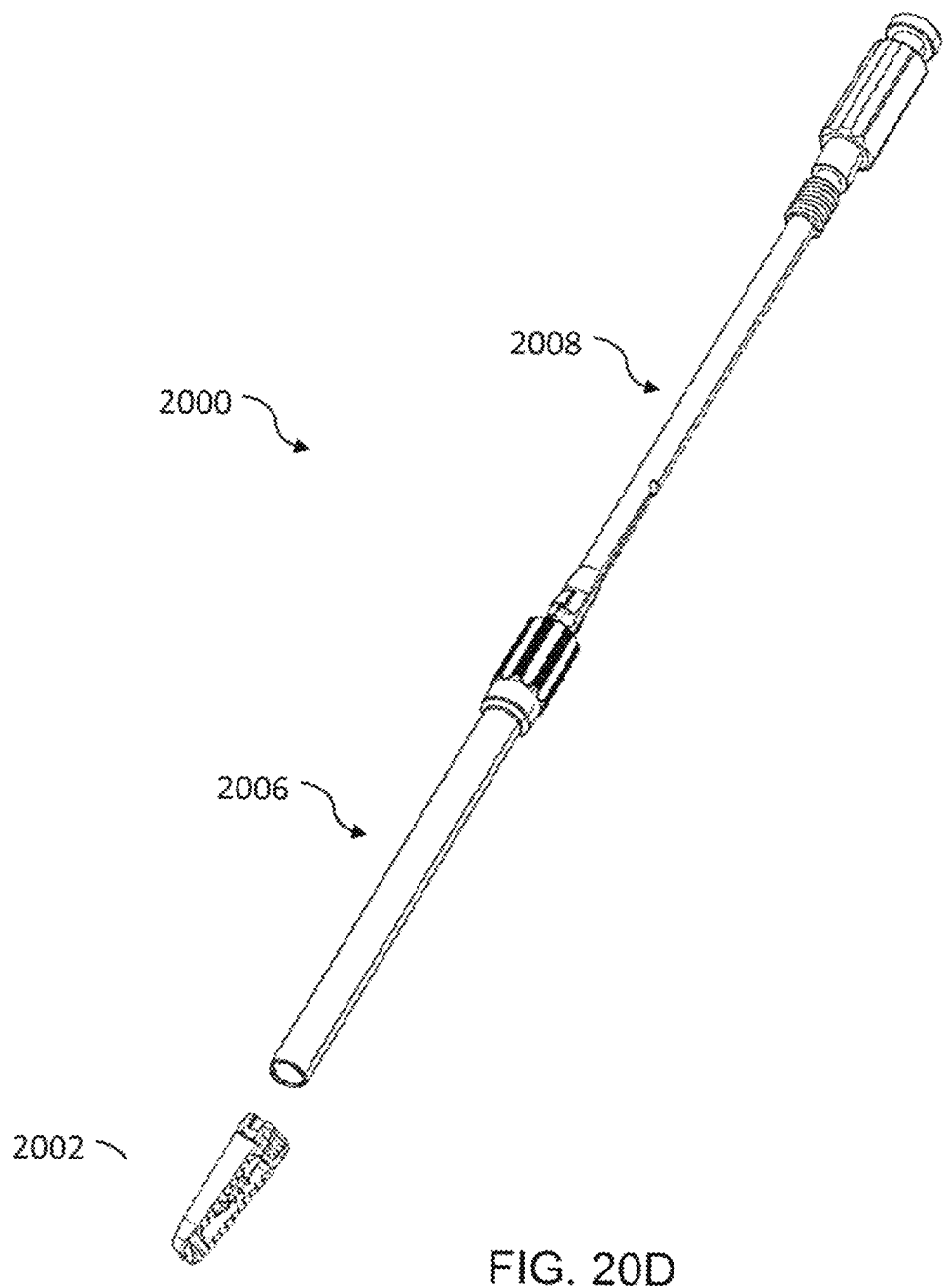
FIG. 20D depicts an exploded view of the axial threaded wedging cage system of FIGS. 20A-20C comprising a delivery instrument.
Figure 22A:
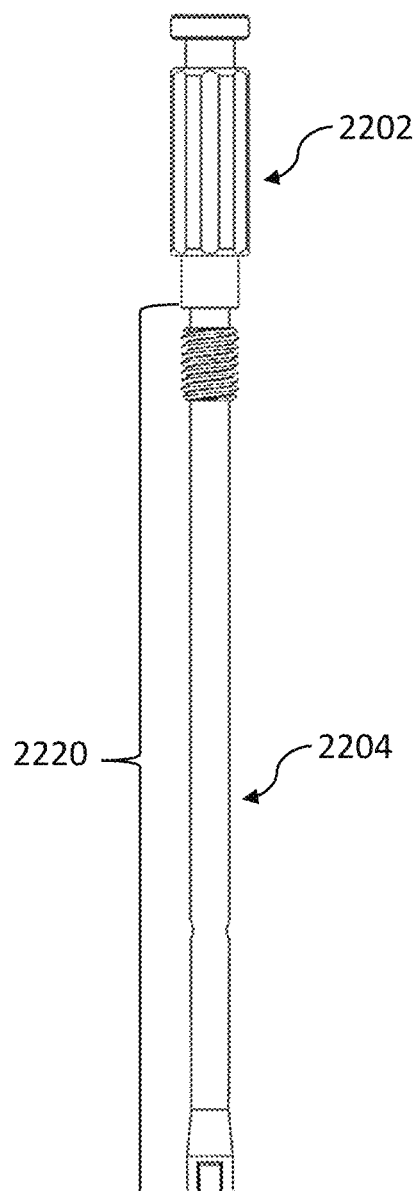
FIGS. 22A-22D depict various views of one embodiment of a insertion cannula.
Figure 22B:
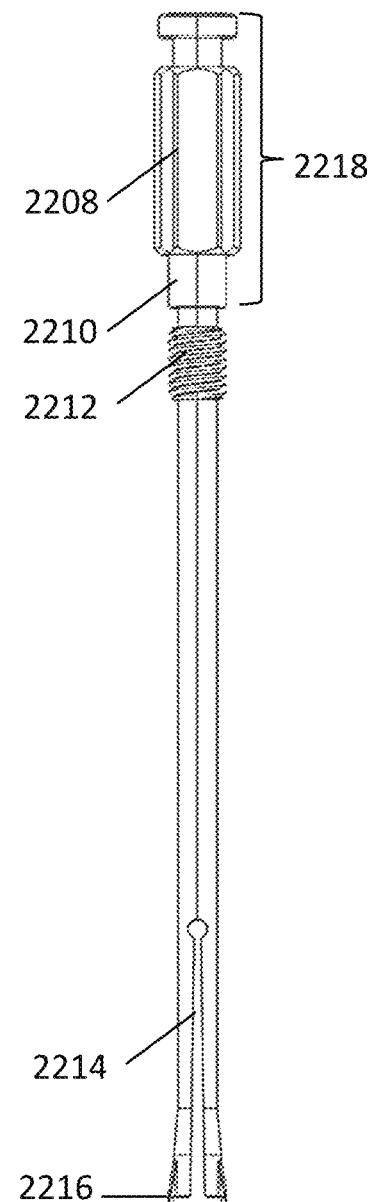
Figure 22C:
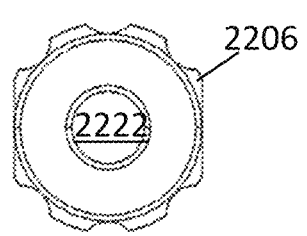
Figure 22D:
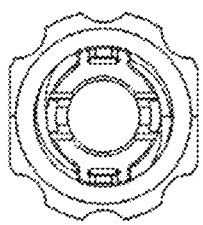
Figures 24A, 24B:
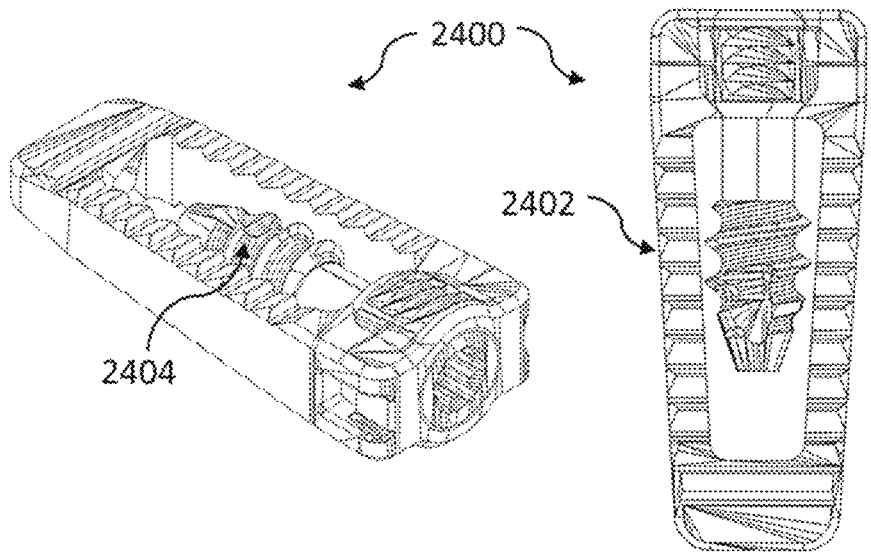
FIGS. 24A-24D depict various views of one embodiment of an axial threaded anchor wedging cage of FIGS. 23A-23D
Figures 24C, 24D:
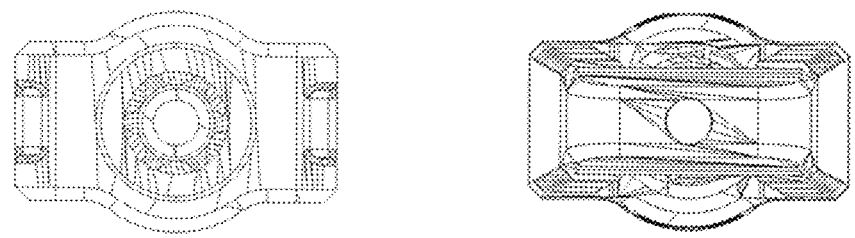

FIGS. 20A-20C depict various views of one embodiment of an SI joint fixation system comprising an axial threaded wedging cage system 2000. The axial threaded wedging cage system 2000 comprises a wedging cage assembly 2002, and an insertion tool assembly 2004 the insertion tool assembly 2004 comprises a guiding cannula 2006 and an insertion cannula 2008 as shown in FIG. 20D. FIG. 20D depicts an exploded view of the axial threaded wedging cage system 2000 of FIGS. 20A-20C;

FIGS. 21A-2D depicts various views of one embodiment of a guiding cannula 2100. The guiding cannula 2100 comprising a handle 2102 and a shaft 2104. The handle 2102 includes a plurality of ribs 2106, the plurality of ribs 2106 are spaced apart and extend circumferentially from the handle 2102. The plurality of ribs 2106 are spaced apart symmetrically or non-symmetrically around the circumference of the handle 2102. The handle 2102 having a length 2118, the plurality of ribs 2106 extend at least portion of the length 2118. The handle 2106 further comprising a counter bore 2110 and internal threads 2112. The plurality of ribs 2106 comprising surface texture or surface roughness to prevent slippage and increase frictional handling. The handle 2102 has a circular or tubular shape.

The shaft 2104 comprising an elongated tube. The elongated tube having an outer diameter (OD), and inner diameter (ID) and a length 2116. The handle having a larger OD than the shaft OD. The guiding cannula 2100 comprising a bore 2114 that extends from a top end to a bottom end. The bore 2114 is sized and configured to receive a portion of the outer diameter of an insertion cannula 2200 (see FIGS. 22A-22E). The internal threads 2112 match or substantially match the external threads 2114 of the insertion cannula 2200.

The insertion cannula 2200 comprises a handle 2202 and a shaft 2204. The handle 2202 includes a plurality of ribs 2206, the plurality of ribs 2206 are spaced apart and extend circumferentially around the handle 2202. The plurality of ribs 2206 are spaced apart symmetrically or non-symmetrically around the circumference of the handle 2202. The handle 2202 having a length 2218, the plurality of ribs 2206 extend at least portion of the length 2218. The plurality of ribs 2206 comprising surface texture or surface roughness (not shown) to prevent slippage and increase frictional handling. The handle 2102 has a circular or tubular shape. The handle 2206 further comprising a first portion 2208 and a second portion 2210. The first portion 2208 outer diameter is greater than the second portion 2210 outer diameter. The first portion 2208 length is greater than the second portion 2210 length. The second portion 2210 is sized and configured to be disposed with the counter bore 2210 of the guiding cannula 2100.

The shaft 2204 comprising an elongated tube. The elongated tube having an outer diameter (OD), and inner diameter (ID) and a length 2118. The handle 2202 having a larger OD than the shaft OD. The insertion cannula 2200 comprising a bore 2222 that extends from a top end to a bottom end. The bore 2222 is sized and configured to receive a portion of the outer diameter of guiding wire (not shown). The handle 2202 having a first end and a second end. At least a portion of the first end comprising external threads 2212, the external threads 2212 is sized and configured to be disposed within the internal threads 2112 of the guiding cannula 2100. At least a portion of the second end comprising at least one elongated slot 2214. The at least one elongated slot 2214 may extend from the second end towards the first end and/or extend towards a portion of the length 220 of the shaft 2204. Alternatively, at least a portion of the second end comprising at least two elongated slots 2214, each of the at least two elongated slots are spaced apart and extend from the second end towards the first end, the spaced apart or spacing is symmetrical, non-symmetrical, and/or on opposite sides. At least a portion of the second end further comprising at least two grippers 2116, the at least two grippers are spaced apart and extend away from the second end or extend beyond a portion of the second end. The spaced apart or spacing is symmetrical, non-symmetrical and/or on opposite sides. The OD of the insertion cannula shaft 2204 is sized and configured to be disposed within the bore 2114 of the guiding cannula 2100.

FIGS. 23A-23D and 24A-24D depict one embodiment of a wedging cage assembly 2400. The wedging cage assembly 2400 comprises a wedging cage 2402 and an axial screw 2404. The wedging cage 2402 may comprise an "A-shaped" wedging cage, a "B-shaped" wedging cage, a "C-shaped" wedging cage, "H-shaped" wedging cage, an "I-shaped" wedging cage, an "O-shaped" wedging cage, an "L-shaped" wedging cage, a "U-shaped" wedging cage, a "M or W-shaped" wedging cage, and/or any combination thereof. In one particular embodiment, the wedging cage 2402 is an "O-shaped" wedging cage. The axial screw having a head, a shaft and threads.

In another embodiment, each of the wedging cages disclosed herein may comprise of different materials that are completely solid or porous. Porosity introduced into the materials allow enhanced bone in-growth and tissue differentiation. More specifically, the porosity elicits a stronger osteogenic response at the cellular response similar to textured or modified surfaces. Alternatively, at least a portion of the wedging cages may comprise of a solid material or a porous material. In addition, at least one surface of the wedging cages may comprise a solid material or a porous material. The porosity may include a plurality of connected, interstitial pores uniformly or non-uniformly distributed throughout the entire wedging cage, and/or at least a portion of the wedging cage. The average interstitial pore size comprises a range of 10 microns to 300 microns. The interstitial pores comprises a shape, the shape may match or substantially match trabecular or coritical pore shapes. Alternatively, the shape may comprise a circle, an oval, a polygon, and irregular polygon, and/or any combination thereof.

In another embodiment, each of the wedging cages disclosed herein may be manufactured from standard manufacturing techniques and/or 3D printing or additive manufacturing techniques. In another embodiment, at least a portion of the wedging cage and/or the entirety of a wedging cage may be manufactured from additive manufacturing methods (AM). Such AM methods include VAT photopolymerization, material jetting, binder jetting, material extrusion or fuse deposition modelling (FDM), power bed fusion (e.g., direct metal laser sintering (DMLS), electron beam melting (EBM), selective heat sintering (SHS), selective laser melting (SLM), selective laser melting (SLS), sheet lamination, and/or directed energy disposition (DED), multi-jet fusion, digital light synthesis, and/or any combination thereof.

VAT polymerization method uses a vat of liquid photopolymer resin, out of which at least a portion of the wedging cage can be constructed layer by layer. An ultraviolet (UV) light is used to cure or harden the resin where required, while a platform moves the structure being made downwards after each new layer is cured.

Material jetting approach can create a structure layer similar to using a two-dimensional ink jet printer. Material is jetted onto a build platform using either a continuous or Drop on Demand (DOD) approach. Material is jetted onto the build surface or platform, where it solidifies and the structure is built layer by layer. Material is deposited from a nozzle which moves horizontally across the build platform. The material layers are then cured or hardened using ultraviolet (UV) light.

The binder jetting approach uses two materials, a powder-based material and a binder. The binder acts as an adhesive between powder layers. The binder is usually in liquid form and the build material in powder form. A print head moves horizontally along the x and y axes of the machine and deposits alternating layers of the build material and the binding material. After each layer, the structure being printed is lowered on its build platform.

Fuse deposition modelling (FDM) is a common material extrusion process and is a technique used in domestic or hobby 3D printers. Material is drawn through a nozzle while under continuous pressure, where it is heated and is then deposited layer by layer into the desired cross-sectional area. The nozzle can move horizontally, and a platform moves up and down vertically after each new layer is deposited. Then the layers are fused together upon deposition as the material is in its melted state.

Powder bed fusion (PBF) methods use either a laser or electron beam to melt and fuse material powder together. All PBF processes involve the spreading of the powder material over previous layers into desired cross-sections. The powders are sintered, layer by layer. The platform lowers the structure to add additional layers, accordingly.

Directed Energy Deposition (DED) is a complex printing process commonly used to repair or add additional material to existing components. A typical DED machine consists of a nozzle mounted on a multi axis arm, which deposits melted material onto the specified surface and cross-section, where it solidifies. The process is similar in principle to material extrusion, but the nozzle can move in multiple directions and is not fixed to a specific axis. The material, which can be deposited from any angle due to 4 and 5 axis machines, is melted upon deposition with a laser or electron beam. The process can be used with polymers, ceramics but is typically used with metals, in the form of either powder or wire. Both conventional and additive manufacturing methods may be used together to create the desired structure pads, and/or any combination thereof.

FIGS. 27A-27I depict isometric views of different embodiments of an SI joint fixation system comprising a 3D printed wedging cage. The 3D printed wedging cage may comprise an A-shaped, a B-shaped, a C-shaped, H-shaped, I-shaped, L-shaped, O-shaped, U-shaped, a Y-shaped, and M or W shaped wedging cage and/or any combination thereof.

At least a portion of the 3D printed wedging cage comprises porosity 2402, 2404. The porosity 2402, 2404 may include a plurality of connected, interstitial pores uniformly or non-uniformly distributed throughout the entire wedging cage. The interstitial pores comprising a shape, the shape may match or substantially match trabecular or cortical patterns or shapes. Alternatively, the interstitial pores may have a shape, the shape may comprise a circle, an oval, a regular polygon or irregular polygon shape. The SI joint fixation system further comprises a screw (not shown), the screw is a fixation screw and/or an axial screw. The SI joint fixation system further comprises a delivery instrument (not shown), the delivery instrument includes a sleeve and an insertion cannula.

In another embodiment, the 3D printed wedging cage comprises a base 2706 and at least one longitudinal member 2708. At least a portion of the base 2706 comprises porosity 2402, 2404. The porosity 2402, 2404 may include a plurality of connected, interstitial pores uniformly or non-uniformly distributed throughout the entire wedging cage. The interstitial pores comprising a shape, the shape may match or substantially match trabecular or cortical patterns or shapes. Alternatively, the interstitial pores may have a shape, the shape may comprise a circle, an oval, a regular polygon or irregular polygon shape.

In another embodiment, the 3D printed wedging cage comprises a base 2706 and at least one longitudinal member 2708. At least a portion of the at least one longitudinal member 2708 comprises porosity 2402, 2404. The porosity 2402, 2404 may include a plurality of connected, interstitial pores uniformly or non-uniformly distributed throughout the entire wedging cage. The interstitial pores comprising a shape, the shape may match or substantially match trabecular or cortical patterns or shapes. Alternatively, the interstitial pores may have a shape, the shape may comprise a circle, an oval, a regular polygon or irregular polygon shape.

In another embodiment, the 3D printed wedging cage comprises a base 2706 and at least one longitudinal member 2708. At least a portion of the base 2706 and the at least one longitudinal member 2708 comprises porosity 2402, 2404. The porosity 2402, 2404 may include a plurality of connected, interstitial pores uniformly or non-uniformly distributed throughout the entire wedging cage. The interstitial pores comprising a shape, the shape may match or substantially match trabecular or cortical patterns or shapes. Alternatively, the interstitial pores may have a shape, the shape may comprise a circle, an oval, a regular polygon or irregular polygon shape.

Figure 27A:
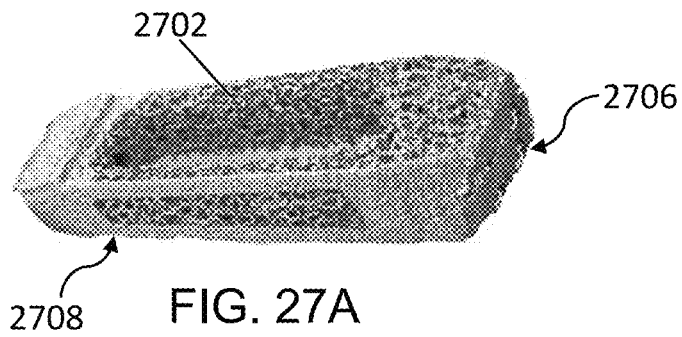
FIGS. 27A-27I depicts isometric views of different embodiments of 3D printed wedging cages.
Figure 27B:
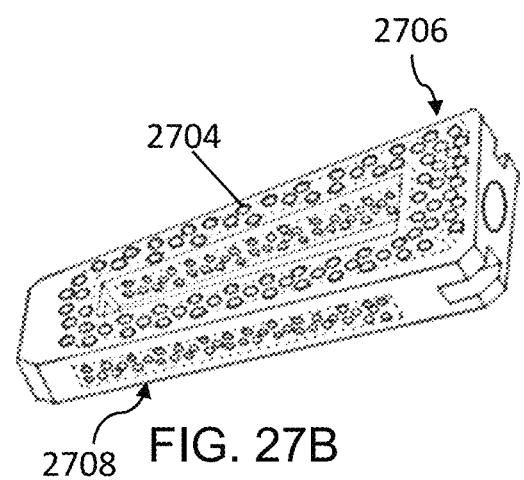
Figure 27C:
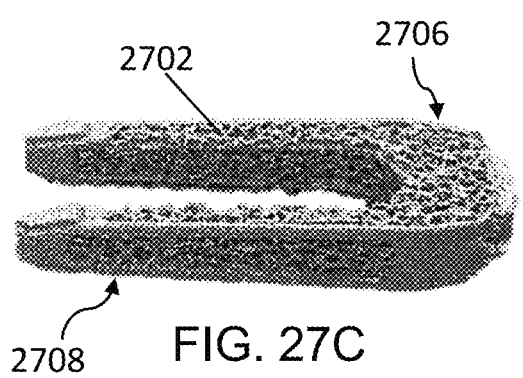
Figure 27D:
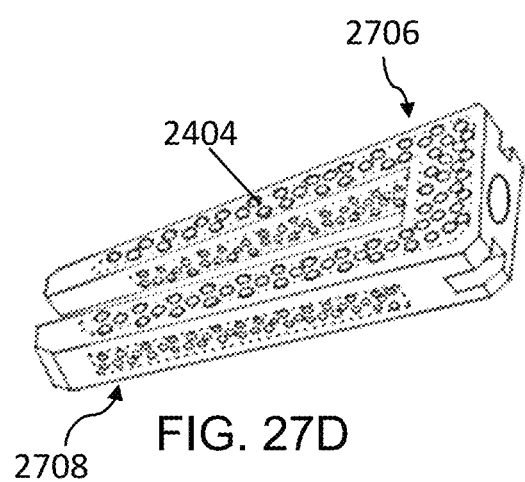
Figure 27E:
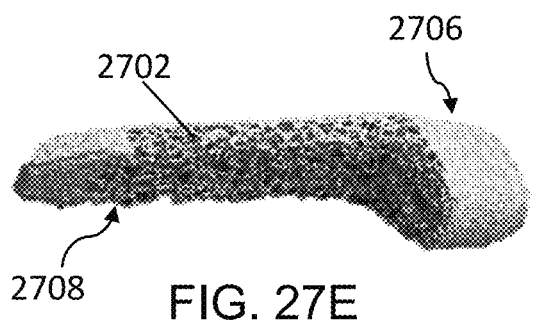
Figure 27F:
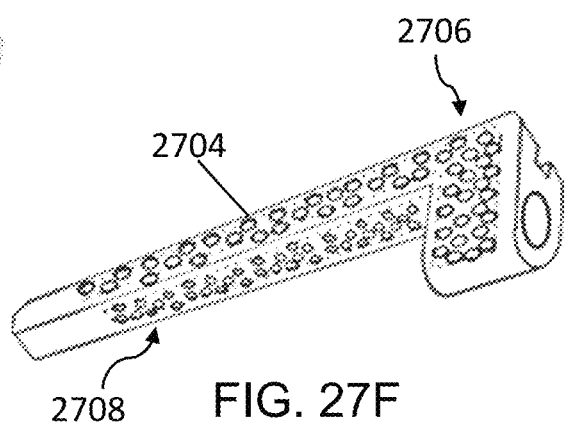
Figure 27G:
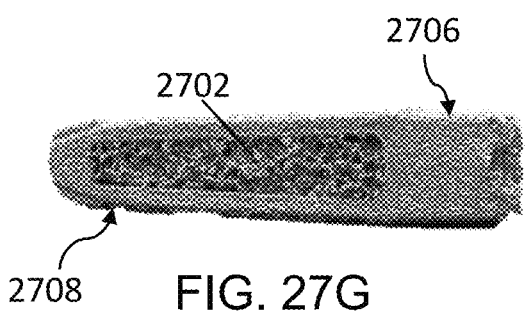
Figure 27H:
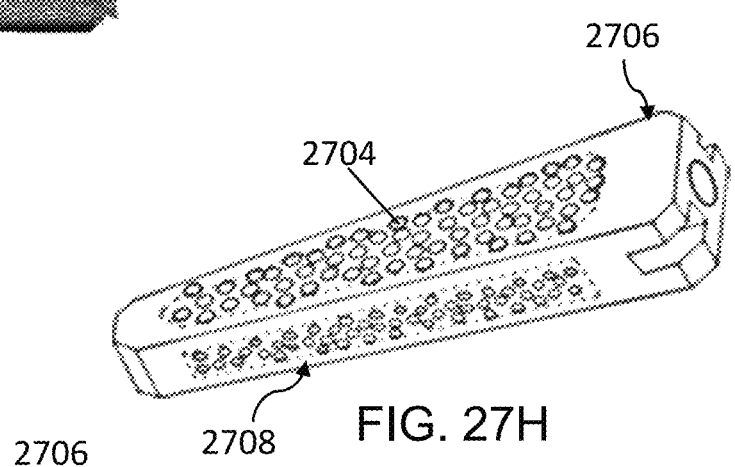
Figure 27I:
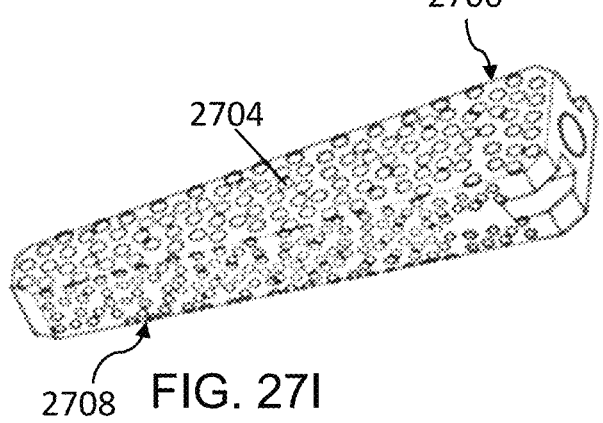

In another embodiment, the 3D printed wedging cage comprises a base 2706 and at least one longitudinal member 2708. The entire base and/or the entire at least one longitudinal member 2708 comprises porosity 2402, 2404 as shown in FIG. 27I. The porosity 2402, 2404 may include a plurality of connected, interstitial pores uniformly or non-uniformly distributed throughout the entire wedging cage. The interstitial pores comprising a shape, the shape may match or substantially match trabecular or cortical patterns or shapes. Alternatively, the interstitial pores may have a shape, the shape may comprise a circle, an oval, a regular polygon or irregular polygon shape.

In another embodiment, the 3D printed wedging cage comprises a base 2706 and at least one longitudinal member 2708. The entire base and/or the entire at least one longitudinal member 2708 comprises a solid cross-section. Solid comprises a material that is not hollow.

FIGS. 29A-29F depict front views of the different embodiments of SI fixation system comprising different shaped wedging cages. The wedging cages comprise an A-shaped wedging cage 2900, a B-shaped wedging cage 2902, a C-shaped wedging cage 2904, and H-shaped wedging cage 2906, an I-shaped wedging cage 2908, L-shaped wedging cage 2910, O-shaped wedging cage, U-shaped wedging cage, a Y-shaped wedging cage, and M or W shaped wedging cage. In one embodiment, the SI joint fixation system comprising a wedging cage 2900, 2902, 2904, 2906, 2908, 2910 comprises a base 2920 and a first longitudinal member 2922. The base having a bore, a top surface and a bottom surface. The first longitudinal member 2922 extending from a bottom surface of the first longitudinal member 2922. The first longitudinal member 2922 may be positioned adjacent or proximate to the perimeter of the bore, and/or the first longitudinal member 2922 may be aligned or aligned concentrically with the bore.

The wedging cage 2900, 2902, 2904, 2906, 2908, 2910 may further comprise a second longitudinal member 2924. The first longitudinal member 2922 having a first end and a second end, and/or the second longitudinal member 2924 having a first end and a second end. The second longitudinal member 2924 may be positioned adjacent or proximate to the perimeter of the bore and/or on the opposite side of the bore. Alternatively, the second longitudinal member 2924 may be spaced apart from the first longitudinal member 2922, and the first longitudinal member 2922 and the second longitudinal member 2924 extend from the bottom surface of the base 2920. In addition, the first ends of the first longitudinal member 2922 and the second longitudinal member 2924 are coupled to the bottom surface of the base 2920. The first longitudinal member 2922 having a length, the second longitudinal member 2924 having a length, the length of the first longitudinal member 2922 and the second longitudinal member 2924 being the same length or different lengths.

The wedging cage 2900, 2902, 2904, 2906, 2908, 2910 may further comprise a lateral support member 2926. The lateral support member 2926 may be positioned perpendicular or substantially perpendicular to the first longitudinal member 2922 and the second longitudinal member 2924. The lateral support member 2926 may have a width, depth and length. The length may be equal to the spacing or the spaced apart dimension of the first longitudinal member 2922 and the second longitudinal member 2924.

The wedging cage 2900, 2902, 2904, 2906, 2908, 2910 may further comprise a second base 2928. The second base 2928 is positioned at the opposite end of the first longitudinal member 2922 and/or the second longitudinal member 2924. Alternatively, the second base 2928 is positioned at second end of the first longitudinal member 2922 and/or the second longitudinal member 2924. The second base 2928 comprising a bore. The bore of the second base 2928 may align with an axis of the bore of the base 2920.

In one embodiment the SI joint fixation system comprises combinations of different shaped wedging cages. For example, the SI joint fixation system comprises a first L-shaped wedging cage, a second L-shaped wedging cage and an I-shaped wedging cage. The I-shaped wedging cage is positioned between the first and second L-shaped wedging cage to produce an "M or W-shaped" wedging cage. The first and second L-shaped wedging cage are positioned spaced apart as mirror images of each other.

Figures 29A, 29B, 29C:
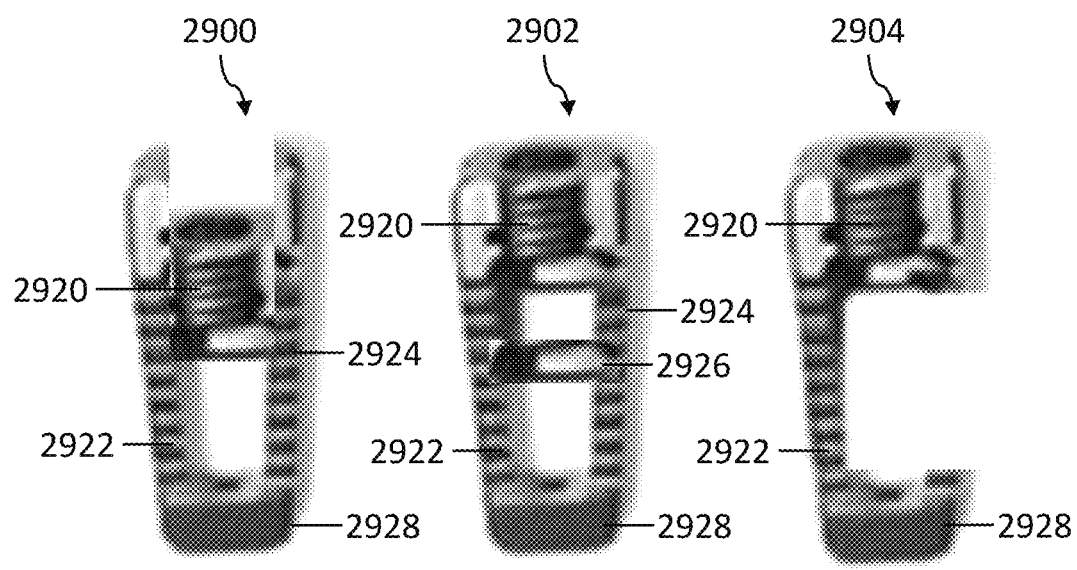
FIGS. 29A-29F depict front views of the different embodiments of wedging cages.
Figures 29D, 29E, 29F:
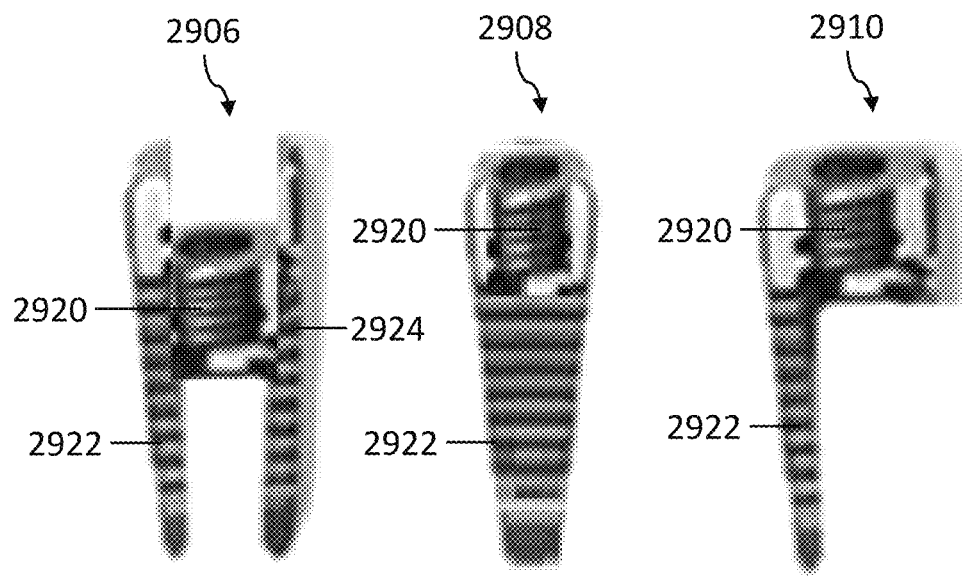

FIG. 29C depicts a front view of one embodiment of an SI joint fixation system comprising a "C-shaped" wedging cage 2904 and a fixation screw (not shown).

Wedging Cage Materials

In various embodiments, the implants and/or portions may comprise silicon nitride and/or various combinations of a variety of surgically acceptable materials, including radiopaque and/or radiolucent materials, other materials or combinations of such materials. Radiolucent materials can include, but are not limited to, polymers, carbon composites, fiber-reinforced polymers, plastics, combinations thereof and the like. Radiopaque materials are traditionally used to construct devices for use in the medical device industry. Radiopaque materials can include, but are not limited to, metal, aluminum, stainless steel, titanium, titanium alloys, cobalt chrome alloys, combinations thereof and the like.

In another embodiment, each of the wedging cages disclosed herein may comprise different materials and/or combinations of materials. The materials may comprise metal, polymer, and/or ceramic. The metals comprise of titanium, steel, tantalum, cobalt-chrome, cobalt-chrome alloys, titanium alloy, nitinol and/or any combination thereof. Polymeric materials comprise PEEK. Ceramic materials comprise alumina, zirconia, silicon nitride, vitoss bone graft substitute, vitrium, and/or any combination thereof.

In another embodiment, the wedging cages disclosed herein can include a silicon nitride material (i.e., $Si_3N_4$ and/or chemical analogues thereof) in their construction, either in the entirety of the implant as well as components, portions, layers and/or surfaces thereof. The incorporation of silicon nitride as a component material for spinal or other implants can provide significant improvements over existing implant materials and material designs currently available, as the silicon nitride material(s) will be highly osteo-inductive and/or osteoconductive and will desirably facilitate and/or promote implant fixation to adjacent living bone surfaces, while concurrently reducing and/or inhibiting periprosthetic infection and/or bacterial adhesion to the surfaces and/or interior portions of the implant.

In various applications, the utility of silicon nitride as an implant material can be enhanced by the addition of various other medical materials, including the use of one or various combinations of titanium, chrome cobalt, stainless steel, silicone, poly (ether ether ketone) (PEEK), ultra-high molecular-weight polyethylene (UHMWPE), polyurethane foams, polylactic acid, apatites and/or various 3D printed materials. In such cases, the employment of such material mixtures in implant construction may enhance the strength and/or durability of a desired implant design, as well as allow for improved surgical outcomes and/or greatly reduced complication rates.

Silicon nitride ($Si_3N_4$) and its various analogs can impart both antibacterial and osteogenic properties to an implant, including to bulk $Si_3N_4$ as well as to implants coated with layers of $Si_3N_4$ of varying thicknesses. In bone replacement as well as prosthetic joint fusion and/or replacement, osseous fixation of implants through direct bone ingrowth (i.e., cementless fixation) is often preferred, and such is often attempted using various surface treatments and/or the incorporation of porous surface layers (i.e., porous Ti6Al4V alloy) on one or more bone-facing surfaces of an implant. Silicon nitride surfaces express reactive nitrogen species (RNS) that promote cell differentiation and osteogenesis, while resisting both gram-positive and gram-negative bacteria. This dual advantage of RNS in terms of promoting osteogenesis, while discouraging bacterial proliferation, can be of significant utility in a variety of implant designs.

Desirably, the inclusion of silicon nitride components into a given implant design will encompass the use of bulk silicon nitride implants, as well as implants incorporating other materials that may also include silicon nitride components and/or layers therein, with the silicon nitride becoming an active agent of bone fusion. RNS such as N2O, NO, and —OONO are highly effective biocidal agents, and the unique surface chemistries of Si3N4 facilitate its activity as an exogenous NO donor. Spontaneous RNS elution from Si3N4 discourages surface bacterial adhesion and activity, and unlike other direct eluting sources of exogenous NO, Si3N4 elutes mainly NH4+ and a small fraction of NH3 ions at physiological pH, because of surface hydrolysis and homolytic cleavage of the Si—N covalent bond. Ammonium NH4+ can enter the cytoplasmic space of cells in controlled concentrations and through specific transporters, and is a nutrient used by cells to synthesize building-block proteins for enzymes and genetic compounds, thus sustaining cell differentiation and proliferation. Together with the leaching of orthosilicic acid and related compounds, NH4+ promotes osteoblast synthesis of bone tissue and stimulates collagen type 1 synthesis in human osteoblasts. Conversely, highly volatile ammonia NH3 can freely penetrate the external membrane and directly target the stability of DNA/RNA structures in bacterial cells. However, the release of unpaired electrons from the mitochondria in eukaryotic cells activates a cascade of consecutive reactions, which starts with NH3 oxidation into hydroxylamine NH2OH (ammonia monooxygenase) along with an additional reductant contribution leading to further oxidation into NO2- nitrite through a process of hydroxylamine oxidoreductase. This latter process involves nitric oxide NO formation. In Si3N4, the elution kinetics of such nitrogen species is slow but continuous, thus providing long-term efficacy against bacterial colonies including mutants (which, unlike eukaryotic cells, lack mitochondria). However, when slowly delivered, NO radicals have been shown to act in an efficient signaling pathway leading to enhanced differentiation and osteogenic activity of human osteoblasts. Desirably, Si3N4 materials can confer resistance against adhesion of both Gram-positive and Gram-negative bacteria, while stimulating osteoblasts to deposit more bone tissue, and of higher quality.

Where the presence of bulk silicon nitride implant materials may not be desired and/or may be impractical for some reason, it may be desirous to incorporate modules and/or layers (such as surface and/or subsurface layers) including silicon nitride on other materials. Silicon nitride structures and/or components can be formed using a variety of techniques, including by compressing, milling and firing silicon nitride powder, as well as by extruding silicon nitride into sheet, tube, pipe and/or thread form (which may be further processed into thread or "rope" by braiding and/or other techniques). Silicon nitride shapes may also be manufactured using subtractive manufacturing techniques (i.e., machining, milling and/or surface roughening), as well as by using additive manufacturing techniques (i.e., surface coating, brazing, welding, bonding, deposition on various material surfaces and/or even by 3D laser printing of structures). If desired, silicon nitride may even be formed using curing or other light/energy activation techniques, such as where a slurry of liquid polymer and silicon nitride particles may be UV cured to create a 3-dimensional structure and/or layer containing silicon nitride. In various embodiments, silicon nitride may be utilized in block form, in sheets, columns and bars, in cable or braided form, in mesh form, in a textured surface coating, in powder form, in granular form, in gel, in putty, in foams and/or as a surface filler and/or coating. In some cases, a surface layer of silicon nitride may be formed on an external and/or internal surface of an implant.

For example, in some embodiments it may be desirous to laser-sinter a thin layer of silicon nitride material (i.e., powder) to the surface of another material, such as PEEK or titanium. One exemplary starting micrometric powder used for laser-sintering of a Si3N4 coating in this manner could comprise a 90 wt % fraction of Si3N4 powder mixed with a 6 wt % of yttrium oxide (Y2O3) and a 4 wt % of aluminum oxide (Al2O3). If desired, a Vision LWI VERGO-Workstation equipped with a Nd:YAG laser with a wavelength of 1064 nm (max pulse energy: 70 J, peak power 17 kW, voltage range 160-500 V, pulse time 1-20 ms, spot size 250-2000 μm) can be utilized to achieve densification of successive layers of Si3N4 powder placed on a water-wet surface of a Titanium substrate in a nitrogen environment, which desirably limits Si3N4 decomposition and oxidation. In the exemplary embodiment, the Nd:YAG laser can be pulsed with a spot size of 2 mm, and driven by an applied voltage of 400 V with a pulse time of 4 ms. This operation can be repeated until a continuous thickness of 15 μm (±5 μm) is formed over an entire surface of the Titanium substrate. This process can create a wavy morphology of the ceramic/metal interface, with interlocks at the micrometer scale between metal and ceramic phases and desirably little or no diffusional transport of the Titanium element into the coating during laser sintering.

In other exemplary embodiments, silicon nitride materials of differing compositions and/or states (i.e., solid, liquid and/or flowable or moldable "slurry" states, for example) could be utilized in a single implant and/or portions thereof, including the use of solid silicon nitride for a base or cage for an implant or wedge, and/or the employment of a moldable silicon nitride "paste" placed within a centrally positioned "graft chamber" of a titanium or PEEK implant.

In various embodiments, the materials may comprise properties that would desirably include improvements or enhancements to the wedging cages disclosed herein, these include one or more of the following: (1) Flexibility in manufacturing and structural diversity, (2) Strong, tough and reliable constructs, (3) Phase stable materials, (4) Favorable imaging characteristics through radiopaqueness, (5) Hydrophilic surfaces and/or structures, (6) Osteoconductive, (7) Osteoinductive, and/or (8) Anti-Bacterial characteristics and/or bacteriostatic.

SI Wedging Cage Methods

The SI joint fixation system is adaptable to variety uses for treatment of SI joint dysfunction via fixation and fusion techniques. The SI joint fixation system may comprise a wedging cage and axial screw, a wedging cage and fixation screw, and a wedging cage (provided alone to be used in conjunction with standard fusion or fixation instrumentation). The SI joint fixation system may be used with open surgical techniques and/or minimally invasive techniques. The minimally invasive techniques comprise an anterior and/or posterior approach.

Figure 25A:
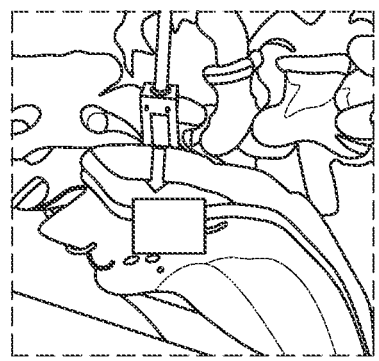
FIGS. 25A-25C illustrates one embodiment of a method to implant the SI joint wedging cage system.
Figure 25B:
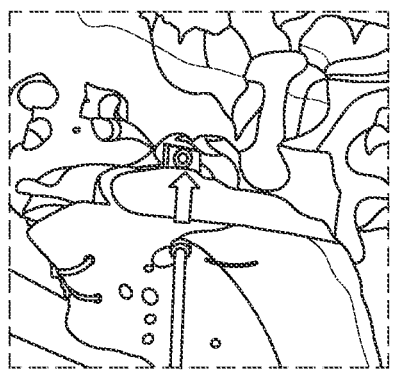
Figure 25C:
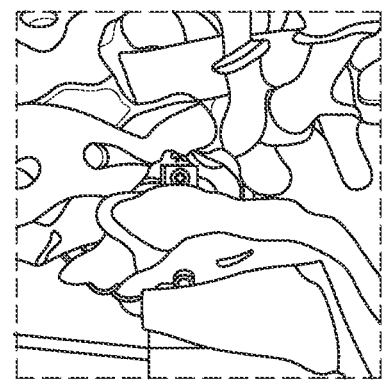

In one embodiment, the SI joint fixation system may be adapted to be deployed before the fixation screws are implanted as shown in FIGS. 25A-25C. The method comprises the steps of placing the patient under general anesthesia, cutting a small incision over the lower back and muscles are gently moved to the side, drilling a small hole through the ilium to access the joint, clearing the sacroiliac joint of ligaments and muscles; deploying the SI joint fixation system into the SI joint; deploying the fixation screws through the SI joint and the SI joint fixation system to encourage bone growth; repositioning muscles into place, and closing the surgical site using standard sutures.

Figure 26A:
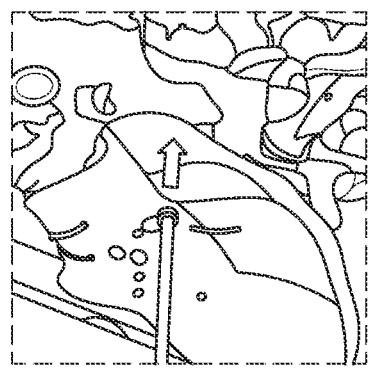
FIGS. 26A-26C illustrates an alternate embodiment of a method to implant the SI joint wedging cage system.
Figure 26B:
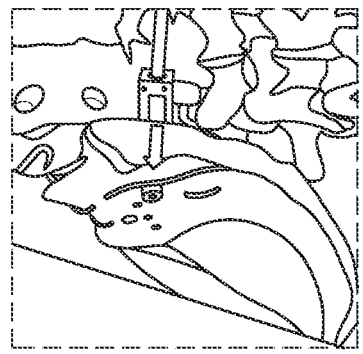
Figure 26C:
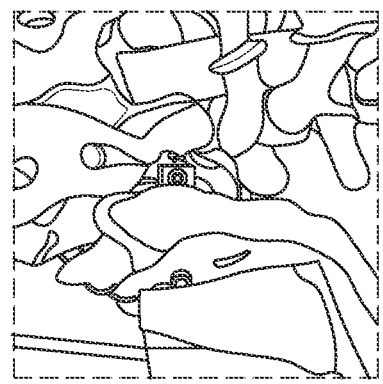

The SI joint fixation system may be adapted to be deployed after the fixation screws are implanted as shown in FIGS. 26A-26C. The method comprises the steps of placing the patient under general anesthesia, cutting a small incision over the lower back and muscles are gently moved to the side, drilling a small hole through the ilium to access the joint, clearing the sacroiliac joint of ligaments and muscles; deploying the fixation screws through the SI joint, deploying the SI joint fixation system onto the fixation screws to encourage bone growth; repositioning muscles into place, and closing the surgical site using standard sutures.

While embodiments and applications of the present subject matter have been shown and described, it would be apparent that other embodiments, applications and aspects are possible and are thus contemplated and are within the scope of this application.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context

We claim:

1. An SI joint fusion system comprising:
a wedging cage, the wedging cage comprising a first base, a first longitudinal member and a second longitudinal member, the first base including a top surface, a bottom surface and a threaded bore, the first longitudinal member including a first proximal end and a first distal end, the first distal end of the first longitudinal member extending away from a portion of the bottom surface of the first base, the second longitudinal member including a second proximal end and a second distal end, the second distal end of the second longitudinal member extending away from a portion of the bottom surface of the first base, the first distal end of the first longitudinal member being spaced apart from the second distal end of the second longitudinal member with an opening formed therebetween at the first and second distal ends, the threaded bore extending from the top surface of the base through the bottom surface of the base; and
a screw, the screw comprising a head, a shank portion and a threaded portion,
the opening between the first and second distal ends being sized to allow the screw to pass between the first and second distal ends.

2. The SI joint fusion system of claim 1, wherein the first longitudinal member is positioned adjacent to a perimeter of the threaded bore.

3. The SI joint fusion system of claim 1, wherein the first longitudinal member and the second longitudinal member are spaced apart along their entire lengths.

4. The SI joint fusion system of claim 3, wherein the wedging cage comprises a second base, the second base being positioned proximate to a midpoint of the first longitudinal member and the second longitudinal member.

5. The SI joint fusion system of claim 3, wherein the first longitudinal member and the second longitudinal member comprise different lengths.

6. The SI joint fusion system of claim 1, wherein the first base further comprises a first channel and a second channel, the first and second channel positioned on opposite sides of the base.

7. The SI joint fusion system of claim 1, wherein the first longitudinal member comprises at least one bone contacting surface, at least a portion of the at least one bone contacting surface including a smooth or textured surface.

8. The SI joint fusion system of claim 3, wherein the first longitudinal member and the second longitudinal member each comprise at least one bone contacting surface, at least a portion of the at least one bone contacting surface of each member including a smooth or textured surface.

9. The SI joint fusion system of claim 3, wherein the first longitudinal member comprises a first plurality of apertures and the second longitudinal member comprises a second plurality of apertures.

10. An SI joint fusion system comprising:
a first base and a first longitudinal member, the first base including a top surface, a bottom surface, and a threaded bore, the first longitudinal member extending away from a first portion of the bottom surface of the first base to a first distal end, the bottom surface of the first base and an inner surface of the first longitudinal member partially enclosing a central space, the central space having an open front surface and an open back surface, each positioned substantially transverse to an implant plane extending through a height dimension of the system, wherein the system comprises an implant plane extending through the first base and the first longitudinal member, the central space having an open peripheral edge substantially aligned with the implant plane extending through the first base and the first longitudinal member, the threaded bore extending from the top surface of the base through the bottom surface of the, base.

11. The SI joint fusion system of claim 10, further comprising a second longitudinal member extending along the implant plane extending through the first base and the first longitudinal member, the second longitudinal member extending away from a portion of the bottom surface of the first base, the first longitudinal member and the second longitudinal member being spaced apart.

12. The SI joint fusion system of claim 11, further comprising a second base.

13. The SI joint fusion system of claim 10, wherein the first base further comprises a first channel and a second channel, the first and second channel positioned on opposite sides of the base.

14. The SI joint fusion system of claim 11, wherein the first longitudinal member and the second longitudinal member each comprise at least one bone contacting surface, at least a portion of each of the at least one bone contacting surfaces including a smooth or textured surface.

15. The SI joint fusion system of claim 10, wherein the first longitudinal member comprises a plurality of apertures.

16. The SI joint fusion system of claim 10, wherein the SI joint fusion system further comprises a screw, the screw comprising a head, a shank portion and a threaded portion, the screw being inserted into the threaded bore.

17. The SI joint fusion system of claim 16, wherein the screw comprises a fixation screw or axial screw.

18. The SI joint fusion system of claim 10, further comprising an anchor, the anchor being rotatable between a retracted position and a deployed position.

19. The SI joint fusion system of claim 18, wherein the anchor comprises a shaft, a first blade and a second blade, the first and second blade extend outwardly from the shaft and are spaced apart.

20. The SI joint fusion system of claim 10, wherein the first longitudinal member is positioned adjacent to a perimeter of the threaded bore.

* * * * *